United States Patent
Aisenbrey et al.

(10) Patent No.: US 12,123,026 B2
(45) Date of Patent: Oct. 22, 2024

(54) HUMAN PLURIPOTENT STEM CELL-DERIVED BRAIN ORGANOIDS FOR CANCER MODELING AND DRUG SCREENING

(71) Applicant: Wisconsin Alumni Research Foundation, Madison, WI (US)

(72) Inventors: Elizabeth Anne Aisenbrey, Madison, WI (US); William Leo Murphy, Waunakee, WI (US); Elizabeth Emma Torr, Madison, WI (US); Victoria Harms, Madison, WI (US); Gaurav Kaushik, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 602 days.

(21) Appl. No.: 16/831,017

(22) Filed: Mar. 26, 2020

(65) Prior Publication Data

US 2020/0318075 A1    Oct. 8, 2020

Related U.S. Application Data

(60) Provisional application No. 62/828,161, filed on Apr. 2, 2019.

(51) Int. Cl.
*C12N 5/09* (2010.01)
(52) U.S. Cl.
CPC ........ *C12N 5/0693* (2013.01); *C12N 2500/50* (2013.01); *C12N 2501/734* (2013.01); *C12N 2501/998* (2013.01); *C12N 2502/086* (2013.01); *C12N 2502/088* (2013.01); *C12N 2502/28* (2013.01); *C12N 2502/30* (2013.01)
(58) Field of Classification Search
CPC .............. C12N 5/0693; C12N 2500/50; C12N 2501/734; C12N 2501/998; C12N 2502/086; C12N 2502/088; C12N 2502/28; C12N 2502/30
See application file for complete search history.

(56) References Cited

U.S. PATENT DOCUMENTS

| | | |
|---|---|---|
| 2016/0186135 A1 | 6/2016 | Thomson |
| 2016/0186137 A1 | 6/2016 | Thomson |
| 2016/0186146 A1* | 6/2016 | Thomson ............. C12N 5/0619 702/19 |

FOREIGN PATENT DOCUMENTS

EP        3129494 B1 *  9/2019   .............  A61K 47/42

OTHER PUBLICATIONS

Lancaster et al., Cerebral organoids model human brain development and microencephaly. Nature, vol. 501 (2013) pp. 373-379 (Year: 2013).*
Linkous et al., Modeling patient-derived glioblastoma with cerebral organoids. Cell Reports (Mar. 19, 2019) pp. 3203-3211.e5 (Year: 2019).*
Chen, G., et al. "Chemically defined conditions for human iPSC derivation and culture." Nature methods 8.5 (2011): 424.
Drury, J. L., et al. "Hydrogels for tissue engineering: scaffold design variables and applications." Biomaterials 24.24 (2003): 4337-4351.
Ebert, A. D., et al. "Induced pluripotent stem cells from a spinal muscular atrophy patient." Nature 457.7227 (2009): 277-280.
Hoffman, A. S. "Hydrogels for biomedical applications" Adv. Drug Deliv. Rev 54 (2002): 3-12.
Howden, S. E., et al. "Genetic correction and analysis of induced pluripotent stem cells from a patient with gyrate atrophy." Proceedings of the National Academy of Sciences 108.16 (2011): 6537-6542.
Lévesque, S. G., et al. "Synthesis of cell-adhesive dextran hydrogels and macroporous scaffolds." Biomaterials 27.30 (2006): 5277-5285.
Long, G. V., et al. "Dabrafenib in patients with Val600Glu or Val600Lys BRAF-mutant melanoma metastatic to the brain (BREAK-MB): a multicentre, open-label, phase 2 trial." The lancet oncology 13.11 (2012): 1087-1095.
Nguyen, K. T., et al. "Photopolymerizable hydrogels for tissue engineering applications." Biomaterials 23.22 (2002): 4307-4314.
Sampson, J. H., et al. "Demographics, prognosis, and therapy in 702 patients with brain metastases from malignant melanoma." Journal of neurosurgery 88.1 (1998): 11-20.
Schwartz, M. P., et al. "Human pluripotent stem cell-derived neural constructs for predicting neural toxicity." Proceedings of the National Academy of Sciences 112.40 (2015): 12516-12521.
Stewart, R., et al. "Comparative RNA-seq analysis in the unsequenced axolotl: the oncogene burst highlights early gene expression in the blastema." PLoS computational biology 9.3 (2013). E1002936.
Wang H (2018) "Modeling neurological diseases with human brain organoids" Front. Synaptic Neurosci. 10:15.
Yu, J., et al. "Human induced pluripotent stem cells free of vector and transgene sequences." Science 324.5928 (2009): 797-801.

* cited by examiner

Primary Examiner — Kara D Johnson
(74) Attorney, Agent, or Firm — Quarles & Brady, LLP

(57) ABSTRACT

The present invention relates to substantially planar vascularized brain cancer organoid and methods of using such vascularized brain cancer organoids in anti-cancer drug discovery screen. In particular, provided herein are methods of producing and using complex, highly uniform vascularized brain cancer organoids that comprise physiologically relevant human cells and have the high degree of sample uniformity and reproducibility required for use in high-throughput screening applications.

16 Claims, 8 Drawing Sheets
(7 of 8 Drawing Sheet(s) Filed in Color)
Specification includes a Sequence Listing.

FIG. 3

↑ indicates increased expression/activity, ↓ indicates decreased expression/activity

| Drug | Target | Therapy Assign. biomarker | Supp. Results Biomarker* | PD Markers* | References | Mechanism of Action |
|---|---|---|---|---|---|---|
| Vemurafenib | BRAF^V600E | BRAF mut | | ↓pMEK ↓pErk | 4, 5 | Target RAS/RAF/MAPK oncogenic pathway in tumor cells with BRAF V600E mutation |
| Dabrafenib | | | | | 15 | |
| Trametinib | MEK | NRAS mut, NF-1 mut | ↑pErk | ↓pErk | 15, 20 | Target RAS/RAF/MAPK oncogenic pathway in tumor cells independent of BRAF mutational status. Often used in clinic in combination with BRAF^V600E inhibitors. |
| Cobimetinib | | | | | 36, 37 | |
| Selumetinib | | | | | 38, 39 | |
| Ribociclib | CDK4 CDK6 | All cases | ↑Ki67 | ↓Ki67 ↓pH3 ↓pRB1 | 40, 41 | Inhibit cell replication |
| Palbociclib | | | | | 42, 43 | |
| Abemaciclib | | | | | 44, 45 | |
| AMG232 | MDM2 | TP53 wt | MDM2 amp, ↑MDM2/4 | ↑p53, ↑p21 | 47, 48 | Activate p53 tumor suppressor |
| Navitoclax | BCL-2/XL | ↑BCL-2 | NO MCL1 amp, ↓MCL1, ↑BCL-XL | ↑Cl.PARP, ↑TUNEL | 49-53 | Inhibit cell survival |
| AZD8186 | PI3Kbeta | PTEN mut or del | PI3K path mut, ↓PTEN, ↓pAKT | ↓pAKT, ↓pS6 | 54, 55 | Inhibit PI3K oncogenic pathway |
| AZD1775 | Wee1 | TP53 mut | DDR path. mut, ↑γH2AX | ↑γH2AX, ↑pH3 | 60-63 | Induce replication stress |

SEQUENCE LISTING

<160> NUMBER OF SEQ ID NOS: 9

<210> SEQ ID NO 1
<211> LENGTH: 14
<212> TYPE: PRT
<213> ORGANISM: Artificial Sequence
<220> FEATURE:
<223> OTHER INFORMATION: synthetic -continued

```
<400> SEQUENCE: 1

Lys Cys Gly Gly Pro Gln Gly Ile Trp Gly Gln Gly Cys Lys
1               5                   10

<210> SEQ ID NO 2
<211> LENGTH: 5
<212> TYPE: PRT
<213> ORGANISM: Artificial Sequence
<220> FEATURE:
<223> OTHER INFORMATION: synthetic

<400> SEQUENCE: 2

Cys Arg Gly Asp Ser
1               5

<210> SEQ ID NO 3
<211> LENGTH: 4
<212> TYPE: PRT
<213> ORGANISM: Artificial Sequence
<220> FEATURE:
<223> OTHER INFORMATION: synthetic

<400> SEQUENCE: 3

Arg Gly Asp Ser
1

<210> SEQ ID NO 4
<211> LENGTH: 5
<212> TYPE: PRT
<213> ORGANISM: Artificial Sequence
<220> FEATURE:
<223> OTHER INFORMATION: synthetic

<400> SEQUENCE: 4

Arg Gly Asp Ser Cys
1               5

<210> SEQ ID NO 5
<211> LENGTH: 6
<212> TYPE: PRT
<213> ORGANISM: Artificial Sequence
<220> FEATURE:
<223> OTHER INFORMATION: synthetic

<400> SEQUENCE: 5

Cys Cys Arg Gly Asp Ser
1               5

<210> SEQ ID NO 6
<211> LENGTH: 6
<212> TYPE: PRT
<213> ORGANISM: Artificial Sequence
<220> FEATURE:
<223> OTHER INFORMATION: synthetic

<400> SEQUENCE: 6

Cys Cys Cys Arg Gly Asp
1               5

<210> SEQ ID NO 7
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: MOD_RES
```

```
<222> LOCATION: (1)..(1)
<223> OTHER INFORMATION: ACETYLATION

<400> SEQUENCE: 7

Cys Arg Gly Asp Ser
1               5

<210> SEQ ID NO 8
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (5)..(5)
<223> OTHER INFORMATION: AMIDATION

<400> SEQUENCE: 8

Cys Arg Gly Asp Ser
1               5

<210> SEQ ID NO 9
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: AMIDATION

<400> SEQUENCE: 9

Cys Arg Gly Asp Ser
1               5
```

HUMAN PLURIPOTENT STEM CELL-DERIVED BRAIN ORGANOIDS FOR CANCER MODELING AND DRUG SCREENING

CROSS-REFERENCE TO RELATED APPLICATIONS

This application claims the benefit of U.S. Provisional Application No. 62/828,161, filed on Apr. 2, 2019, which is incorporated by reference herein as if set forth in its entirety.

STATEMENT REGARDING FEDERALLY FUNDED RESEARCH OR DEVELOPMENT

This invention was made with government support under TR002383 awarded by the National Institutes of Health. The government has certain right in the invention.

REFERENCE TO A SEQUENCE LISTING SUBMITTED VIA EFS-WEB

The content of the ASCII text file of the sequence listing named "960296_04012_ST25.txt" which is 2.04 kb in size was created on Mar. 25, 2020 and electronically submitted via EFS-Web herewith the application is incorporated herein by reference in its entirety.

BACKGROUND

Brain metastases, which are cancer cells that have spread from the primary tumor to the brain, are the most common intracranial tumors and are associated with high morbidity and mortality. Lung cancer, breast cancer, and melanoma most frequently develop brain metastases, with brain tumors being present in 75% of melanoma patient autopsies. The current standard for assessing drug efficacy of brain metastasis relies primarily on the patient's response to therapeutics and often requires many rounds of trial-and-error treatment. An alternative method is a patient-derived xenograft (PDX), in which a biopsy of human tumor is implanted into a rodent model and screened for multiple treatments; however, this is not representative of a human tissue microenvironment. As a result, improved systems and methods for modeling human cancers and assessing therapeutic efficacy in vitro are of interest. Such systems would also be applicable as in vitro model systems for understanding brain cancers that arise directly in the brain cells, without metastatic invasion from a different tissue of origin, and for assessing the impact of therapeutic interventions on such cancers and on cells of the brain.

SUMMARY OF THE DISCLOSURE

In a first aspect, provided herein is a method of producing a substantially planar vascularized brain cancer organoid. The method can comprise or consist essentially of (a) contacting a mixed human cell population comprising neural progenitor cells, endothelial cells, pericytes, and microglia to a substantially planar hydrogel, wherein the hydrogel comprises an RGD-containing peptide and a matrix metalloproteinase (MMP)-sensitive peptide; (b) culturing the contacted hydrogel for at least 7 days until a hydrogel comprising neurons, glia, and vasculature is obtained; (c) contacting cancer cells to the cultured hydrogel of (b); and (d) culturing the cancer cell-contacted hydrogel under culture conditions that promote cancer cell proliferation, whereby a vascularized brain cancer organoid comprising a plurality of cancer cells is obtained. The plurality of cancer cells can form a tumor on or within the hydrogel. The cancer cells can comprise lung cancer cells, breast cancer cells, melanoma, colon cancer cells, pancreatic cancer cells, or prostate cancer cells, or a mixture thereof. The neural progenitor cells, endothelial cells, pericytes, or microglia can be derived from human pluripotent stem cells. The human pluripotent stem cells can be embryonic stem cells or induced pluripotent stem cells. The hydrogel can comprise polymerized polyethylene glycol (PEG). The PEG can be 8 arm PEG norbornene (tripentaerythritol). The hydrogel can have a shear modulus of between about 100 Pa to about 1600 Pa. The RGD-containing peptide can be selected from the group consisting of CRGDS (SEQ ID NO:2), RGDS (SEQ ID NO:3), RGDSC (SEQ ID NO:4), CCRGDS (SEQ ID NO:5), CCCRGD (SEQ ID NO:6), Ac-CRGDS (SEQ ID NO:7), CRGDS-CONH(2) (SEQ ID NO:8), and Ac-CRGDS-CONH(2) (SEQ ID NO:9). The MMP-sensitive peptide can be SEQ ID NO:1.

In another aspect, provided herein is a substantially planar vascularized brain cancer organoid obtained according to the methods described herein.

In a further aspect, provided herein is a method of producing a substantially planar vascularized brain cancer organoid. The method can comprise or consist essentially of (a) on day zero, contacting a plurality of human cells to a substantially planar hydrogel, wherein the hydrogel comprises an RGD-containing peptide and a matrix metalloproteinase (MMP)-sensitive peptide, the plurality of human cells comprising one or more of human endothelial cells (EC) and pericytes (PC) at day 0; (b) culturing the contacted hydrogel for about 6 to about 8 days, and then adding human NPCs to the cultured hydrogel; (c) culturing the NPC-containing hydrogel of (b) for about 4 to about 6 days, and then adding human microglia (MG) to the cultured NPC-containing hydrogel; (d) culturing the MG-containing hydrogel of (c) until a vascularized brain organoid comprising neurons, glia, and vasculature is obtained; (e) contacting cancer cells to the brain organoid of (d); and (f) culturing the cancer cell-contacted brain organoid under culture conditions that promote cancer cell proliferation, whereby a vascularized brain cancer organoid comprising a plurality of cancer cells is obtained. The plurality of cancer cells can form a tumor. The cancer cells can comprise lung cancer cells, breast cancer cells, melanoma, colon cancer cells, pancreatic cancer cells, or prostate cancer cells, or a mixture thereof. The neural progenitor cells, endothelial cells, pericytes, or microglia can be derived from human pluripotent stem cells. The hydrogel can comprise polymerized polyethylene glycol (PEG). The RGD-containing peptide can be selected from the group consisting of CRGDS (SEQ ID NO:2), RGDS (SEQ ID NO:3), RGDSC (SEQ ID NO:4), CCRGDS (SEQ ID NO:5), CCCRGD (SEQ ID NO:6), Ac-CRGDS (SEQ ID NO:7), CRGDS-CONH(2) (SEQ ID NO:8), and Ac-CRGDS-CONH(2) (SEQ ID NO:9).

In a further aspect, provided herein is a method of in vitro screening of a test substance. The method can comprise or consist essentially of (a) contacting a test substance to a substantially planar vascularized brain cancer organoid; and (b) detecting an effect of the test substance agent on one or more cell types within the contacted organoid. The effect of the test substance can be anti-cancer activity. The test substance can be a drug, small molecule, hormone, growth factor, binding protein, nucleic acid molecule, peptide, protein, or co-cultured cell. Detecting can comprise detecting at least one effect of the agent on morphology, proliferation, or life span of cancer cells within the contacted organoid, whereby an agent that reduces proliferation or life span of cancer cells or has a negative impact on the morphology of cancers cells is identified as having anti-cancer activity. Detecting can comprise performing a method selected from the group consisting of RNA sequencing, gene expression profiling, transcriptome analysis, metabolome analysis, detecting reporter or sensor, protein expression profiling, Forster resonance energy transfer (FRET), metabolic profiling, and microdialysis. The test substance can be screened for an effect on gene expression and wherein detecting comprises assaying for differential gene expression relative to an uncontacted brain cancer organoid.

In a further aspect, provided herein is a kit for obtaining a substantially planar vascularized brain cancer organoid. The kit can comprise (a) a substantially planar vascularized brain organoid; and (b) instructions for contacting the vascularized brain organoid of (a) with cancer cells obtained from a subject to obtain a substantially planar vascularized brain cancer organoid. The substantially planar vascularized brain organoid can be obtained by (i) contacting a mixed human cell population comprising neural progenitor cells, endothelial cells, pericytes, and microglia to a substantially planar hydrogel comprising an RGD-containing peptide and a matrix metalloproteinase (MMP)-sensitive peptide; and (ii) culturing the contacted hydrogel for at least 7 days until a substantially planar hydrogel comprising neurons, glia, and vasculature is obtained. The kit can further comprise one or more of a negative cancer cell sample and positive cancer cell sample, wherein the negative cancer cell sample comprises a plurality of cancer cells incapable of growing on the vascularized brain organoid, and wherein the positive cancer cell sample comprises a plurality of cancer cells capable of growing on the vascularized brain organoid.

In another aspect, provided herein is a kit for obtaining a substantially planar vascularized brain organoid. The kit can comprise (a) a substantially planar hydrogel comprising an RGD-containing peptide and a matrix metalloproteinase (MMP)-sensitive peptide; (b) a human cell composition comprising human neural progenitor cells, endothelial cells, pericytes, and microglia; and (c) instructions for contacting the human cell composition to the hydrogel and culturing the contacted hydrogel for about 7 days until a substantially planar hydrogel comprising neurons, glia, and vasculature is obtained. The kit can further comprise instructions for contacting the vascularized brain organoid with cancer cells obtained from a subject whereby a substantially planar vascularized brain cancer organoid is obtained. The kit can further comprise one or more of a negative cancer cell sample and positive cancer cell sample, wherein the negative cancer cell sample comprises a plurality of cancer cells incapable of growing on the vascularized brain organoid, and wherein the positive cancer cell sample comprises a plurality of cancer cells capable of growing on the vascularized brain organoid.

These and other features, objects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will be better understood and features, aspects and advantages other than those set forth above will become apparent when consideration is given to the following detailed description thereof. Such detailed description makes reference to the following drawings, wherein:

FIG. 3 is a table listing protein kinase inhibitor drugs to be tested in a metastatic cancer cell-seeded brain organoid.

DETAILED DESCRIPTION

Figure 1:
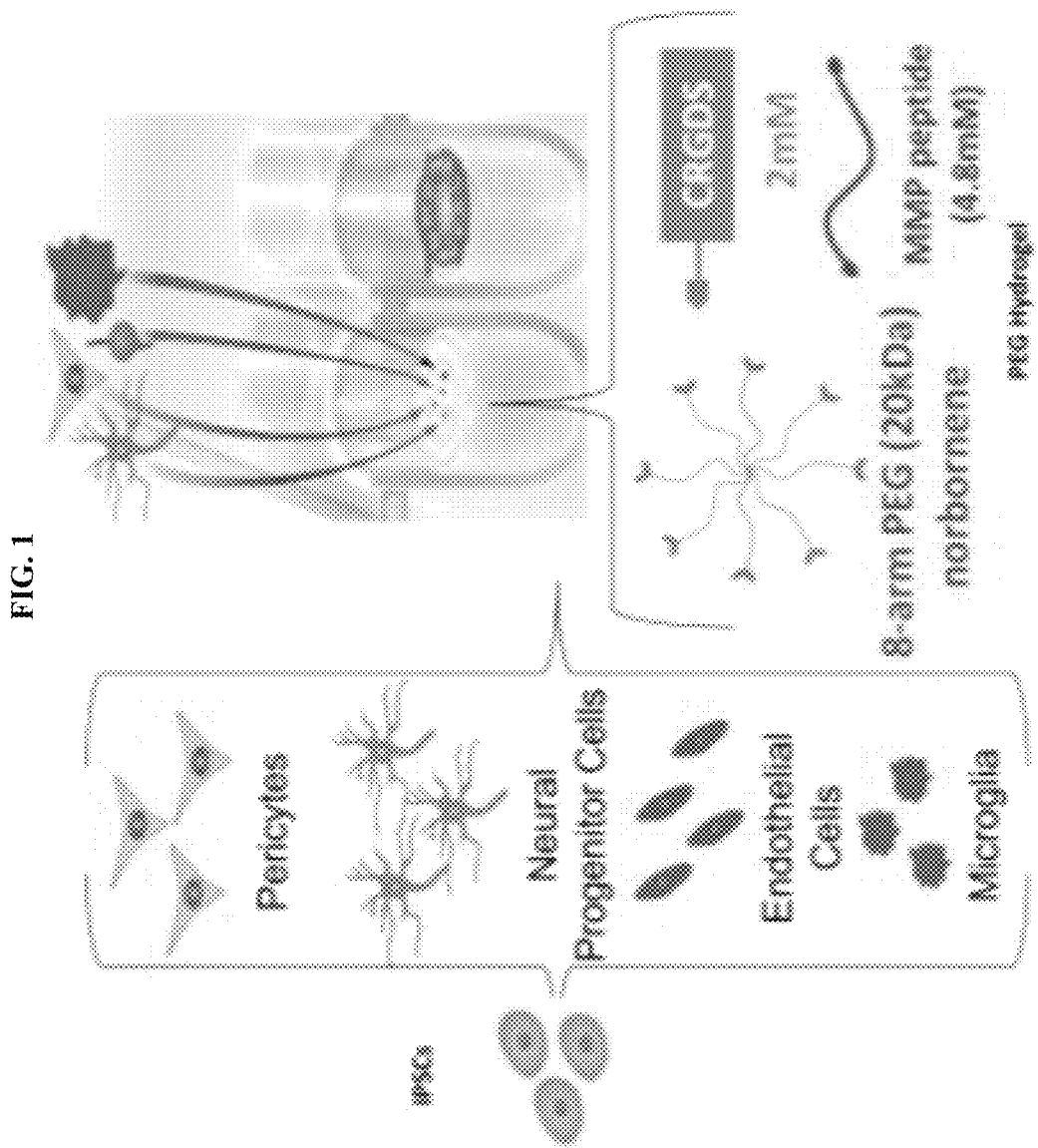
FIG. 1 is a schematic illustrating IPS cell-derived, self-assembled brain organoids comprising PEG hydrogel.

The present invention is based at least in part on the Inventors' development of a planar human vascularized organoid that recapitulates brain tissue and brain-specific cell types. Such organoids, which can be produced using progenitor cell types and differentiated cells obtained from human pluripotent stem cells, are substantially planar sheets that are particularly well suited for imaging, observing, and modeling the infiltration of cancer cells into brain tissue. When infiltrated with cancer cells, the vascularized brain organoid is particularly useful to screen and assess candidate anti-cancer and anti-metastatic therapeutics.

To develop the brain tissue organoids (referred to herein as "brain organoids"), neural progenitor cells (NPCs), endothelial cells (ECs), pericytes, and microglia (MG) are seeded onto hydrogels containing matrix metalloproteinase (MMP)-sensitive peptides and crosslinked RGD-binding peptides. Once seeded onto the hydrogel, the cells differentiate and self-assemble into a 3D vascularized neural matrix. This matrix recapitulates the brain, making it a promising environment to study cancer cell metastasis and to evaluate the effect of different therapeutics on brain cancers. While it was known that human pluripotent stem cell-derived neuronal tissues provide an alternative to animal testing for modeling human brain development, the Inventors developed a complex human brain tissue model that comprises physiologically relevant human cells including cancer cells such as metastatic cancer cells and solid tumors, and have high sample uniformity necessary for large-scale, high-throughput screening applications. By seeding cancer cells, such as metastatic melanoma cells, directly onto a substantially planar vascularized brain organoid, the resulting brain cancer organoid may be studied to elucidate processes involved in metastasis, brain tumor formation, and neurovascular and microglial responses to the presence of metastatic cancer cells. Upon tumor formation, the metastatic brain organoids can be screened for an array of therapeutics and the response of the cancer cells and organoid cells can be monitored. Ultimately, this technology can be used for patient-specific screenings in which brain organoids can be derived from patient-derived iPSCs, seeded with patient-derived cancer cells, biopsy tissue, or tumor organoids, and screened for multiple drugs in a high-throughput fashion.

Compositions

Accordingly, the present invention provides a composition comprising a brain cancer organoid. As used herein, the term, "organoid" refers to an engineered material, produced in vitro, that comprises complex topologies and geometries (e.g., multi-layered structures, segments, sheets, tubes, sacs) that recapitulate in vivo physiological conditions and cell-to-cell interactions found within native tissues. Generally, organoids are prepared in vitro by the addition of various cell types including, but not limited to, some combination of pluripotent, multipotent, differentiated cell types, or isolated organ progenitors, to a biocompatible substrate and, in some cases, self-organization of such cell types within the substrate. Organoids of this disclosure preferably contain cells, topologies, and geometries that recapitulate the mammalian brain, in particular the human brain, and model morphological and biological changes that occur upon invasion of brain tissue by metastatic cancer. In exemplary embodiments of this disclosure, the organoids provide a physiologically relevant microenvironment for analysis or perturbation of cell-cell interactions, cell-matrix interactions, and tissue morphogenesis upon invasion of brain tissue by a metastatic cancer. In such cases, the organoids are "brain cancer organoids." As described herein, these organoids also provide a uniquely advantageous system for screening test substances for anti-cancer and anti-metastatic activity.

In exemplary embodiments, the brain cancer organoid is substantially planar, meaning that it has much greater dimension in two dimensions and a substantially smaller dimension in a third, comparable to a disc, sheet, or other substantially flexible, flat items. In other words, a substantially planar brain organoid has a thickness that is much less than its surface area. Preferably, a substantially planar organoid has a thickness in the range of about 100 micrometers to about 500 micrometers. While substantially planar organoids can have any desired thickness, but thicknesses over 500 micrometers prove difficult for imaging intact organoids. Sectioning of thicker organoids may be required for imaging purposes.

In exemplary embodiments, a substantially planar brain cancer organoid comprises a porous biomaterial such as a hydrogel. The term "hydrogel" refers to a highly hydrated porous material comprising synthetic or biological components formed when an organic polymer (natural or synthetic) is cross-linked via covalent, ionic, or hydrogen bonds to create an open-lattice structure that entraps water molecules to form a gel. Generally, hydrogels are hydrophilic, but do not dissolve in water. In addition, hydrogels are mimetics of extracellular matrix and are commonly formed from polymeric precursors such as, for example, polyethylene glycol monomers and peptide crosslinkers. Hydrogels appropriate for constructing 3D brain cancer organoids include, without limitation, synthetic hydrogels, bioactive hydrogels, biocompatible hydrogels, cytocompatible hydrogels, chemically defined hydrogels, chemically-defined synthetic hydrogels, and proteolytically degradable hydrogels. As used herein, the term "cytocompatible" means the hydrogel material is substantially non-cytotoxic and produces no, or essentially no, cytotoxic degradation products. As used herein, the term "proteolytically degradable" means that hydrogel comprises crosslinked elements that can be cleaved enzymatically or non-enzymatically to break down the material. Illustrative enzymatically degradable linkages include peptidic linkages cleavable by metalloproteinases and collagenases.

Hydrogels appropriate for use in a brain cancer organoid of this disclosure include without limitation, polyethylene glycol (PEG), polyvinyl alcohol (PVA), polyvinyl pyrrolidone (PVP), polyacrylamides, and polysaccharides. PEG is a polymer having solubility in water and in many organic solvents and, generally, lacking toxicity, antigenicity, or immunogenicity. Proteins and cells exhibit little to no intrinsic adhesion or interaction with PEG hydrogels. See Drury & Mooney, Biomaterials 24(24):4337-51 (2003); Nguyen & West, Biomaterials 23(22):4307-14 (2002); and Hoffman, Adv. Drug Deliv. Rev. 54(1):3-12 (2002). Thus, PEG provides an ideal "blank slate" upon which one can present specific biological molecules to cells in a controlled manner. PEG can be activated at each terminus to be bifunctional, or just one terminus can be modified to have a reactive moiety. For example, a PEG monomer can be modified to have a relatively inert methoxy moiety (e.g., methoxy-PEG-OH) at one terminus while the other terminus is a hydroxyl group that is readily chemically modifiable. Polysaccharide hydrogels are made by crosslinking natural or semi-synthetic polysaccharides such as alginate, carboxymethylcellulose, hyaluronic acid, and chitosan. The cross-linking reaction allows for the formation of a three-dimensional network made of covalent bonds between the polymer chains—a network that is stable under physiological conditions.

In some cases, the hydrogel is formed using PEG monomers functionalized with norbornene. For example, the hydrogel is prepared using precursors having multiple arms (e.g., 2-100 arms) where each arm has a terminus. In some cases, multi-armed precursors may be dendrimers or other highly branched materials. An arm on a hydrogel precursor refers to a linear chain of chemical groups that connect a crosslinkable functional group to a polymer core. In some cases, the hydrogel precursors are 4-arm or 8-arm PEG monomers reacted with 5-norbornene-2-carboxylic acid to form a norbornene-functionalized 4-arm or 8-arm PEG solution. In some cases, the PEG is 8-arm PEG norbornene (tripentaerythritol). PEG hydrogel formation involves the thiol-ene click chemistry of a norbornene covalently binding with a free thiol crosslinker. As such, multi-arm PEG monomers having different core chemistries (i.e., hexaglycerol, pentaerythriol) functionalized with norbornene reactive groups may be used for the organoid described herein. Additionally, PEG monomers of various molecular weights (for example, 1 kDa-100 kDa) may be used. Altering the PEG hydrogel formulation, including concentration of PEG monomer and crosslinker, number of reactive arms, length of crosslinker, may necessitate additional modifications for brain organoid formation.

Preferably, the hydrogel further comprises a bioactive agent such as a growth factor, a cytokine, a bioactive polypeptide or peptide (e.g., RGD-containing peptides), or any other bioactive ligand capable of interacting with a biomolecule of the cells cultured on or within the hydrogel. In exemplary embodiments, hydrogels comprise peptides having an integrin-binding RGD sequence include, without limitation, CRGDS (SEQ ID NO:2), RGDS (SEQ ID NO:3), RGDSC (SEQ ID NO:4), CCRGDS (SEQ ID NO:5), CCCRGD (SEQ ID NO:6), Ac-CRGDS (SEQ ID NO:7), CRGDS-CONH(2) (SEQ ID NO:8), and Ac-CRGDS-CONH(2) (SEQ ID NO:9). Without being bound by any particular theory or mode of action, the presence of RGD-containing peptides allow for cell adhesion within the hydrogel, which is important for cell culture and organoid formation. Accordingly, one may use other peptides containing a RGD-sequence with a thiol-containing cysteine to tether to the hydrogel network. In addition, one may vary RGD peptide concentration, length, and sequence, as well as degradability and chemistry.

The number and type of appropriate bioactive agents for the present invention will depend on the types of cells cultured on the hydrogel. Examples of suitable bioactive ligands include, without limitation, carboxyl, amine, phenol, guanidine, thiol, indole, imidazole, hydroxyl, sulfate, norbornene, maleimide, laminin, fibronectin, fibrinogen, peptide sequences, or combinations thereof. Bioactive ligands can be covalently incorporated into PEG hydrogels using a thiol-ene-based photo-polymerization strategy. As used herein, "bioactive" is intended to indicate the ability to facilitate a cellular or tissue response, such as differentiation of a pluripotent stem cell, induction of vasculogenesis, neural stem cell differentiation, promotion of cellular attachment, promotion of cell self-assembly, and promotion of cell-cell interactions.

Other PEG formulations may be useful for methods of using the tissue constructs in, for example, screening applications (i.e., screening for an agent having a certain activity or effect on a tumor or cancer cells in a substantially planar brain organoid as provided herein). In some cases, hydrogels are prepared using PEG formulations that comprise non-degradable crosslinkers and/or extracellular matrix-derived peptides or other peptides (e.g., peptides comprising an integrin-binding sequence such as CRGDS (SEQ ID NO:2) and others described herein). For example, dextran hydrogels are produced by introducing primary amine groups for covalent immobilization of extracellular-matrix-derived peptides (Lévesque and Shoichet, Biomaterials 27(30): 5277-85 (2006)). In yet other cases, hydrogels comprise different crosslinking densities or, in some cases, contain crosslinked MMP-degradable (MMP-sensitive) peptides.

Preferably, hydrogels used for the organoids described herein are biocompatible. As used herein, the term "biocompatible" refers to the ability of a material (e.g., hydrogel) to perform as a substrate that will support cellular activity, including the facilitation of molecular and mechanical signaling systems, in order to permit proper cell self-assembly or cellular function such as tissue formation, production of soluble bioactive molecules (e.g., growth factors), or specific cell behaviors such as migration and proliferation. In some cases, "biocompatibility" means the absence of components having cell- or tissue-damaging effects.

Hydrogels can be prepared in any suitable tissue culture vessel that permits production, growth, and maintenance of the brain organoids described herein. For example, hydrogels can be prepared in a multi-well tissue culture vessel such as a 96-well tissue culture plate. A multi-well vessel is advantageous to facilitate mechanization and large-scale or high-throughput screening of brain cancer organoids according to the methods described herein. For example, a substantially planar brain cancer organoid can be prepared or provided using a multi-well tissue culture vessel that facilitates high-throughput assessment of, for example, cellular interactions, in vitro development, toxicity, and cell proliferation upon contacting a chemical compound of interest to the neural construct. Preferably, hydrogels for the brain organoids described herein are prepared in multiple wells of a multi-well tissue culture plate (e.g., a 96-well U-bottom or flat-bottom plate).

Figure 4:
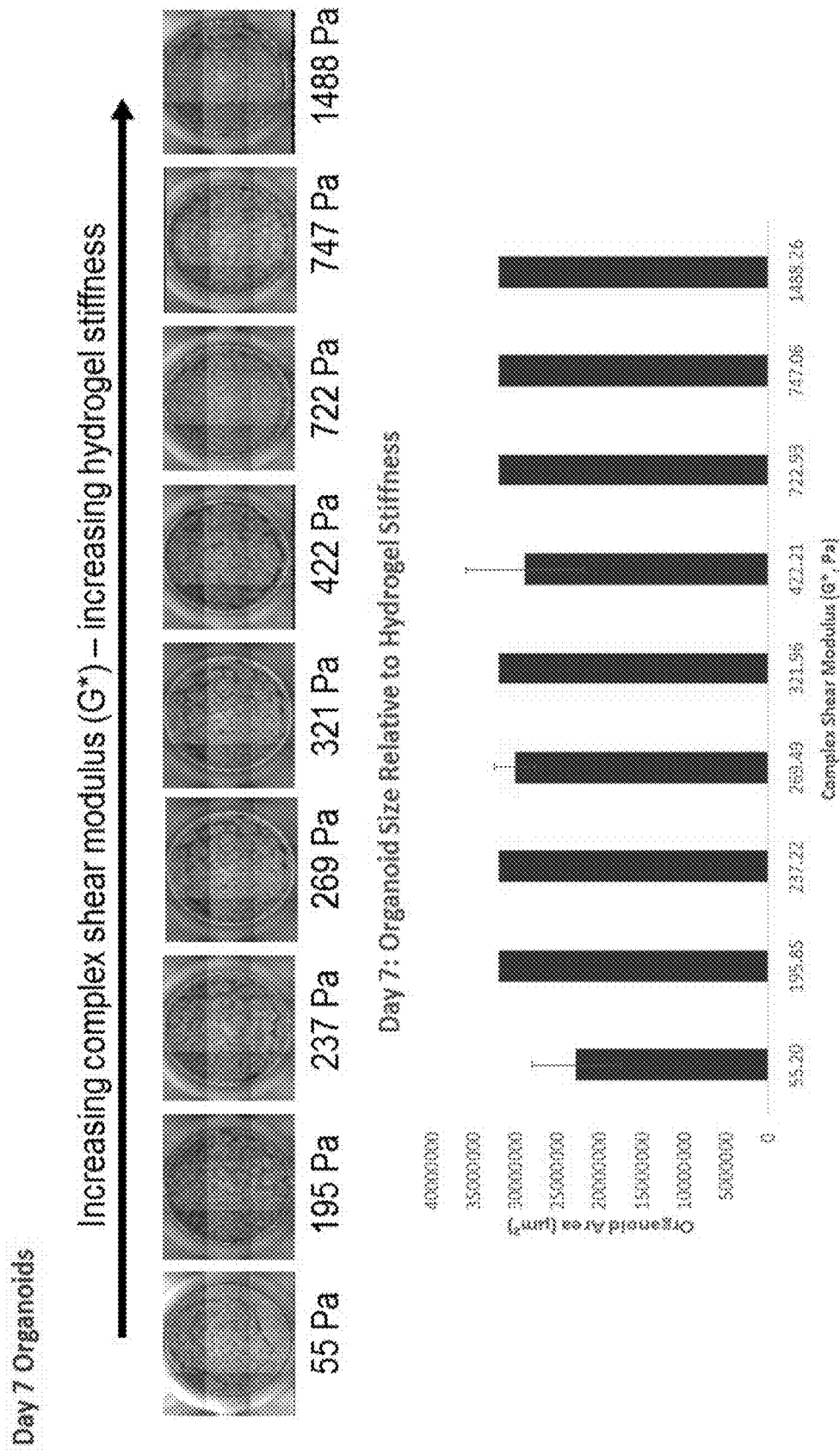
FIG. 4 provides images of Day 7 organoids produced on hydrogels having increasing complex shear moduli (G*). Also provided are sizes of Day 7 organoids produced on hydrogels having increasing complex shear moduli (G*).
Figure 5:
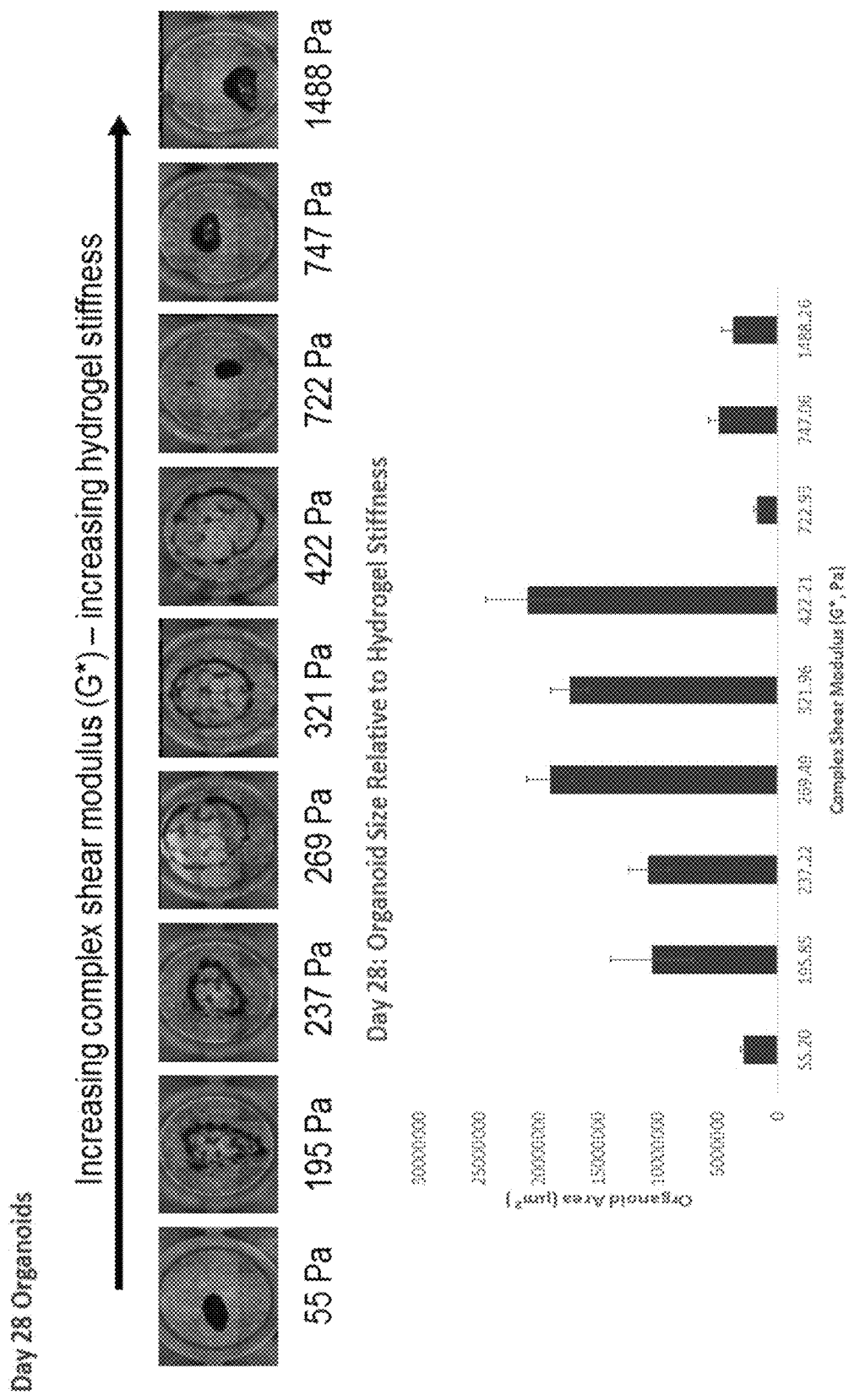
FIG. 5 provides images of Day 28 organoids produced on hydrogels having increasing complex shear moduli (G*). Also provided are sizes of Day 28 organoids produced on hydrogels having increasing complex shear moduli (G*).
Figure 6:
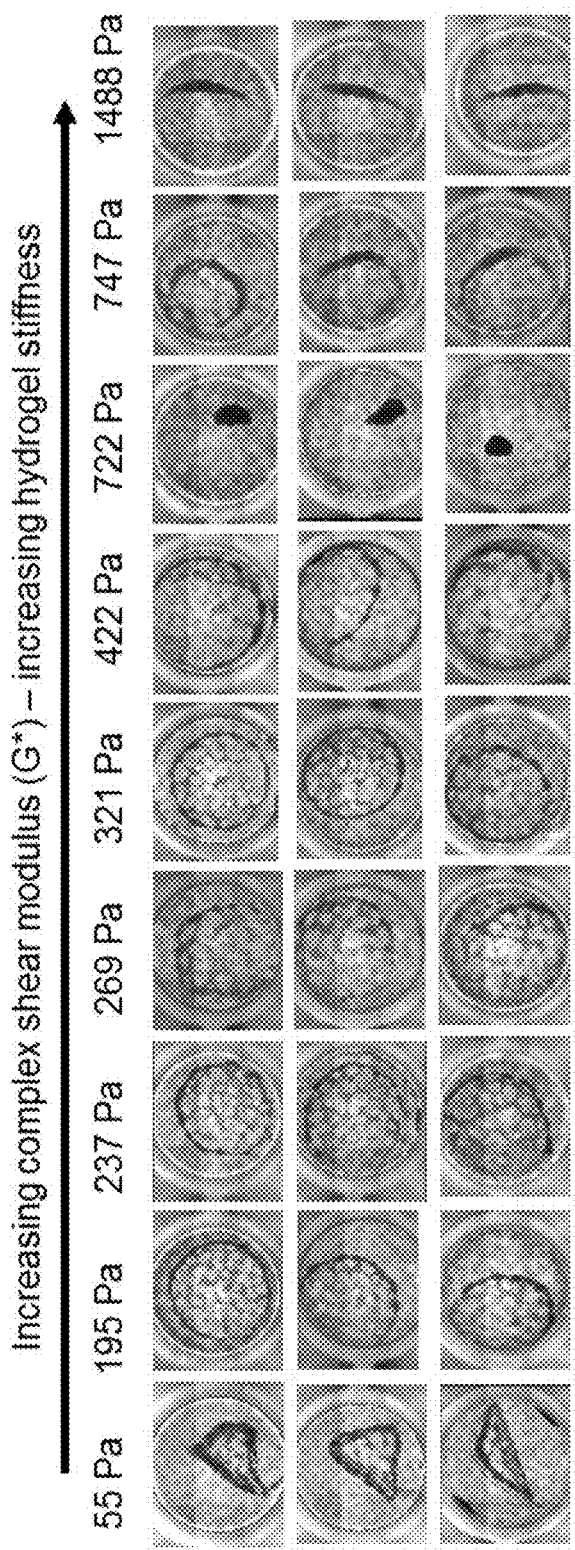
FIG. 6 provides images demonstrating the reproducibility of Day 14 organoids on hydrogels having increasing complex shear moduli (G*).
Figure 7:
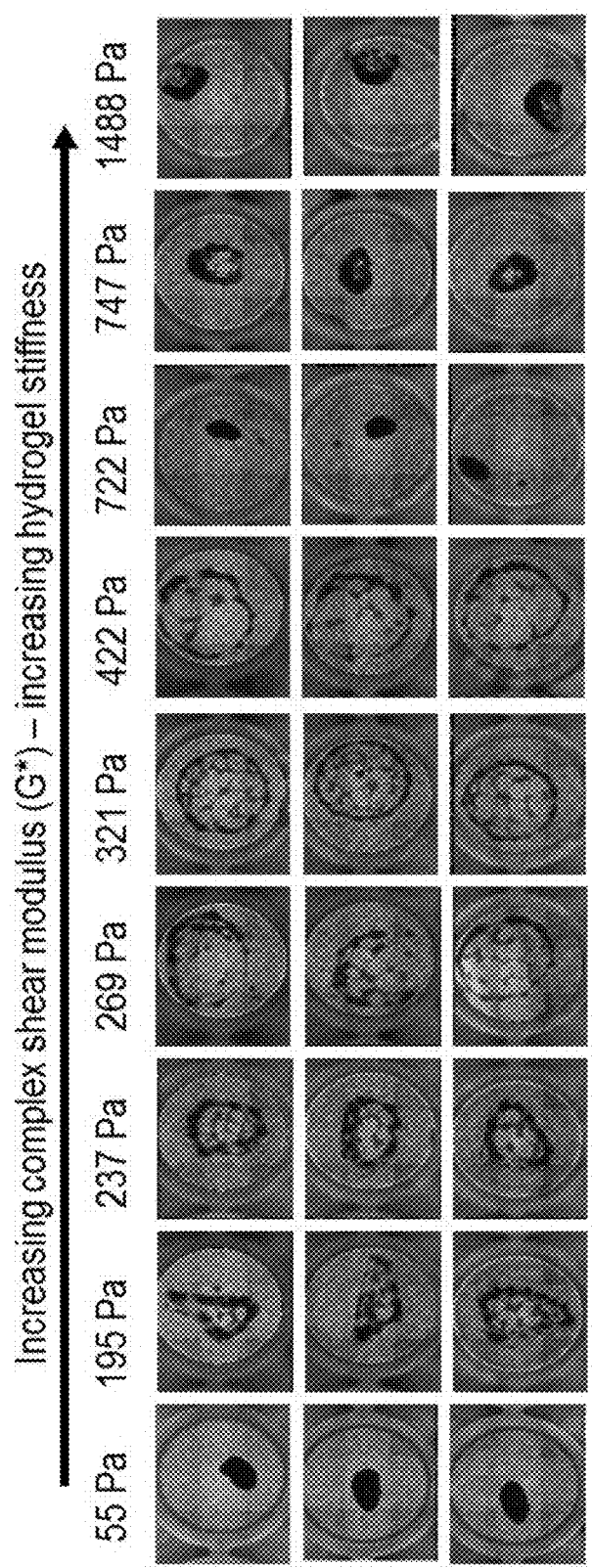
FIG. 7 provides images demonstrating the reproducibility of Day 28 organoids on hydrogels having increasing complex shear moduli (G*).

As described in Example 2, brain organoids of this disclosure can be prepared with hydrogels having varied mechanical properties. For instance, the inventors determined that changes in mechanical stiffness (i.e., shear modulus) of a hydrogel affected organoid morphology and reproducibility of brain organoid characteristics. In particular, variations in shear modulus, which represents mechanical stiffness of a hydrogel, produce morphological changes in the organoids. Referring to FIG. 4, folding of the organoid may be observed starting on day 7. The extent of folding is increased by day 14 as shown in FIG. 6, and folding is especially apparent by day 28 with some organoids becoming much more compact (FIG. 7). These data support a conclusion that hydrogel stiffness is an important factor for production of planar, reproducible organoids. In some cases, it may be advantageous to use a hydrogel having "medium" stiffness hydrogel, which was associated with highly reproducible formation of planar organoids. Shear moduli of "medium" stiffness hydrogels are preferably in a range of about 100 Pa to about 1600 Pa (e.g., 100, 200, 400, 800, 1600 Pa). Preferably, the hydrogel has a shear modulus of about 300 Pa. It will be understood that shear moduli for medium stiffness hydrogels will vary depending on parameters including, without limitation, the type of polymer, composition of polymerization solution, and thickness of the hydrogel. In some cases, a formulation of a medium stiffness hydrogel comprises or consists essentially of 40 mg/ml 8 arm PEG norbornene (tripentaerythritol), 60% Tryp-MMP (GenScript), 2 mM CRGDS peptide (GenScript) 2 mM, and 0.2% Irgacure (prepared in phosphate buffered saline). Any appropriate technique can be used to assess hydrogel stiffness. For example, rheometry (i.e., shear-mode dynamic mechanical analysis) is a convenient method for in situ characterization of hydrogels. A rheometer can used to conduct a dynamic strain sweep test to assess the mechanical properties of hydrogel formulations under different conditions. In Example 2, a 5.5 g force was applied to the samples with parallel plate crossheads and run from 0.005% to 100% strain. Complex shear modulus was calculated as the average of measurements taken at 1 Hz, 2% to 20% strain.

To each hydrogel, a mixture of human cells is added. Preferably, the mixture comprises neural progenitor cells (NPCs), endothelial cells (ECs), pericytes (PCs), and microglia (MG). Some or all of these human cell types can be produced in vitro by differentiating human pluripotent stem cells (e.g., human induced pluripotent stem cells, human embryonic stem cells) accordingly to known differentiation methods. In other cases, primary cells or established cell lines can be used. In exemplary embodiments, human pluripotent stem cells are differentiated in vitro under chemically defined, serum-free, and xenogeneic material-free conditions to separately derive distinct organoid components such as endothelial cells and microglia as previously described by Schwartz et al., *PNAS*. 2015:11:12516-21, incorporated herein by reference as if set forth in its entirety. See also U.S. Publication Nos. 2016/0186137 and 2016/0186135, incorporated herein by reference as if set forth in its entirety.

In some cases, a cell mixture is used to seed a prepared hydrogel. For example, the hydrogel can be seeded with a cell mixture comprising approximately $1 \times 10^5$ neural progenitor cells (NPCs), $8 \times 10^4$ endothelial cells (ECs), $1.6 \times 10^4$ pericytes (PCs), and $2.5 \times 10^3$ microglia (MG). In other cases, the cell mixture for each hydrogel comprises NPCs, ECs, PCs, and MG in the same ratios as listed above but increased or decreased in number depending on the well sizes of the multi-well tissue culture plate used. Provided that the disclosed ratio is maintained, each cell type can be provided for each hydrogel produced in a multi-well tissue culture plate (e.g., a 96-well tissue culture plate) according to the following ranges: NPCs can be added to a hydrogel at a density between about 10,000 cells/well to about 500,000 cells/well (e.g., about 10,000 cells/well; 20,000 cells/well; 30,000 cells/well; 40,000 cells/well; 50,000 cells/well; 75,000 cells/well; 100,000 cells/well; 150,000 cells/well; 200,000 cells/well; 250,000 cells/well; 300,000 cells/well; 400,000 cells/well; 450,000 cells/well; 500,000 cells/well). In some cases, NPCs are seeded at a density between about 50,000 to about 200,000 cells/well. ECs can be added to a hydrogel at a density between about 10,000 cells/well to about 500,000 cells/well (e.g., about 10,000 cells/well; 20,000 cells/well; 30,000 cells/well; 40,000 cells/well; 50,000 cells/well; 80,000 cells/well; 100,000 cells/well; 150,000 cells/well; 200,000 cells/well; 250,000 cells/well; 300,000 cells/well; 400,000 cells/well; 450,000 cells/well; 500,000 cells/well). In some cases, ECs are seeded at a density between about 50,000 to about 100,000 ECs/well. PCs can be added to a hydrogel at a density between about 5,000 cells/well to about 30,000 cells/well (e.g., about 5,000 cells/well; 7,500 cells/well; 10,000 cells/well; 15,000 cells/well; 20,000 cells/well; 25,000 cells/well; 30,000 cells/well). In some cases, PCs are seeded at a density between about 10,000 to about 20,000 PCs/well. MG can be added to a hydrogel at a density between about 100 cells/well to about 5,000 cells/well (e.g., about 100, 150, 200, 250, 300, 350, 400, 450, 500, 550, 600, 650, 700, 750, 800, 850, 900, 950, 1000, 1250, 1500, 1750, 2000, 2250, 2500, 2750, 3000, 3250, 3500, 3750, 4000, 4250, 4500, 4750, 5000 cells/well). In some cases, MG are seeded at a density between about 1,000 to about 3,000 MG/well.

As described in Example 1, cell-seeded hydrogels should be incubated, preferably without medium changes, for about 48 hours at 37° C. with 5% $CO_2$ to permit cell attachment. Following the initial incubation, cell-seeded hydrogels are incubated for at least 7 days at 37° C. with 5% $CO_2$, preferably with daily medium changes, to permit organoid maturation, which includes formation of a vasculature network.

To mature organoids, at least 7 days post-seeding of hydrogels and incubation as described above, cancer cells are added to form substantially planar vascularized brain cancer organoids. In some cases, it may be advantageous to use cancer cells (or a mixture of cancerous and non-cancerous cells) obtained from a patient's biopsied tissue sample or other biological sample (e.g., bone marrow, fluid samples such as blood, plasma, serum, lymph fluid, ascites, and urine). In some cases, cancer cells are obtained from a cancer cell line, a tumor, or a tissue or other biological sample suspected of containing cancer cells. In some cases, the cancer cells have unknown metastatic potential.

In some cases, human cells of a single cell type or mixtures of two or more cell types are added to a hydrogel at the same time, for example on culture day 0. In other cases, it will be advantageous to add one or more human cell types (e.g., NPCs, EC, PCs, MG) at one time-point and then add additional cell types at one or more different time points. By way of non-limiting example, human ECs and PCs can be added to a hydrogel at one time-point (e.g., culture day 0), and then NPCs are added at culture day 7, and MG are added at culture day 12. An exemplary protocol for preparing organoids of this disclosure is set forth in Table 2. The time-points described in this section and Table 2, however, are provided for illustration purposes only and are not intended to be limiting on appropriate timing options that can be used to prepare compositions of this disclosure.

In some cases, a hydrogel is prepared about 24 hours (i.e., about 1 day) prior to an initial seeding with cells. On culture day 0, endothelial cells (ECs) and pericytes (PCs), which are maintained in a culture medium such as E7V, are seeded onto the prepared hydrogel. ECs and PCs can be added at any appropriate cell density. In some cases, seeding comprises contacting about $1 \times 10^4$ to about $3 \times 10^4$ ECs (e.g., about $1 \times 10^4$, $1.5 \times 10^4$, $2 \times 10^4$, $2.5 \times 10^4$, $3 \times 10^4$ ECs) and about $2 \times 10^3$ to about $5 \times 10^3$ PCs (e.g., about $2 \times 10^3$, $2.5 \times 10^3$, $3 \times 10^3$, $3.5 \times 10^3$, $4 \times 10^3$, $4.5 \times 10^3$, $5 \times 10^3$ PCs) to a hydrogel prepared as described in this disclosure in a multiwell plate such as a 96-well plate. The ratios of cell numbers can be maintained and the overall numbers increased or decreased for different well sizes. After seeding with ECs and PCs, the seeded hydrogel can be maintained at an appropriate temperature for culturing such cells (e.g., about 37° C.) for about 48 hours (i.e., about 2 days). Following this incubation period, the culture medium can be removed and replaced with fresh cultured medium. The seeded hydrogel can be cultured for another 4-5 days, whereby the ECs and PCs differentiate and form vascularized tissue within the hydrogel. Such vascularized tissue typically forms within the hydrogels by about Day 7, meaning about 7 days from culture Day 0. On Day 7, neural progenitor cells (NPCs) can be added. In some cases, about $1.5 \times 10^4$ NPCs to about $3.5 \times 10^4$ NPCs (e.g., about $1.5 \times 10^4$, $2 \times 10^4$, $2.5 \times 10^4$, $3 \times 10^4$, $3.5 \times 10^4$ NPCs). The culture medium from this point onwards can be replaced with a neural growth (NG) culture medium. See, for example, Table 5.

Following seeding with NPCs, the seeded hydrogel is incubated at an appropriate temperature for culturing such cells (e.g., about 37° C.) for about 24 hours to about 96 hours (i.e., about 1 day to about 4 days). Following this incubation period, the culture medium can be removed and replaced with a neural growth (NG) culture medium. See, for example, Table 5. On culture Day 12, microglia (MG) are be added at a density between about 100 cells/well to about 5,000 cells/well (e.g., about 100, 150, 200, 250, 300, 350, 400, 450, 500, 550, 600, 650, 700, 750, 800, 850, 900, 950, 1000, 1250, 1500, 1750, 2000, 2250, 2500, 2750, 3000, 3250, 3500, 3750, 4000, 4250, 4500, 4750, 5000 cells/well). Preferably, MG are seeded at a density between about 500 to about 3,000 MG/well. The MG-containing organoids can be allowed to mature for at least 14 days to allow network formation. At this point, cells within the hydrogel have differentiated and organized into a brain organoid. After this point, other cell types, such as cancer cells (e.g., GFP/mCherry-positive or label-free cancer cells), can be added at various densities and cultured to produced brain cancer organoids.

Cancer cells can be prepared, for example, by collecting cancer tissues from patients and culturing the tissues in a cell culture medium under an adherent or floating culture condition. Alternatively, cancer tissues collected from patients can be spheroid-cultured, and then cultured in a cell culture medium under an adherent or floating culture condition. Any culture media or liquids can be used to culture cancer cells. Known basal culture liquids, which are not particularly limited as long as they are suitable for culturing cancer cells include, for example, N2B27, DMEM/F12, DMEM, F10, F12, IMDM, EMEM, RPMI-1640, MEM, BME, Mocoy's 5A, and MCDB131. In brain organoid culture, N2B27 is preferred.

As used herein, the term "cancer" refers to the physiological condition in mammals, which is typically characterized by unregulated cell growth, or such a physiological condition. Herein, cancer types are not particularly limited, and include those listed below. Carcinomas (epithelial cancers) include pancreatic cancer, prostatic cancer, breast cancer, skin cancer, cancers of the digestive tract, lung cancer, hepatocellular carcinoma, cervical cancer, uterine cancer, ovary cancer, fallopian tube cancer, vaginal cancer, liver cancer, bile duct cancer, bladder cancer, ureter cancer, thyroid cancer, adrenal cancer, kidney cancer, and cancers of other glandular tissues. Sarcomas (non-epithelial tumors) include liposarcoma, leiomyosarcoma, rhabdomyosarcoma, synovial sarcoma, angiosarcoma, fibrosarcoma, malignant peripheral nerve sheath tumor, gastrointestinal stromal tumor, desmoid tumor, Ewing's sarcoma, osteosarcoma, chondrosarcoma, leukemia, lymphoma, myeloma, tumors of other parenchymal organs, for example, melanoma and brain tumor.

Of particular interest are cancers having significant potential to undergo a metastasis, which is the spread of cancer to another region distant from the site of the primary cancer. As used herein, "metastasis" refers to the ability of cells of a cancer (e.g. a primary tumor, or a metastasis tumor) to be transmitted to other locations in the body and to establish new tumors at such locations. As used herein, the term "metastatic" refers to a cell that has a potential for metastasis and, when used to prepare brain cancer organoids of this disclosure, is able to seed a tumor or a cell colony of interest. Many primary cancers including, without limitation, skin cancer, breast cancer, colon cancer, lung cancer, pancreatic cancer, and stomach cancer, exhibit significant potential to metastasize and spread from its point of origin (the primary site) to other parts of the body. Metastatic cancers typically enter the bloodstream or lymph system, which can carry them to another part of the body, where they attach to the wall of a blood or lymph vessel and move through it into a new organ. Metastatic cancers must be able to grow and thrive in their new location and avoid attacks from the body's immune system. When a cancer has spread to the brain, the cancer is still named after the site of the primary cancer. For example, "metastatic breast cancer to the brain" refers to breast cancer that spread from breast tissue to the brain.

Although human cells are preferred for use in brain organoids and brain cancer organoids of this disclosure, it may be advantageous in some instances to prepare organoids comprising non-human cells. For example, it may be advantageous to use cells obtained from other mammalian species including, without limitation, equine, canine, porcine, bovine, feline, caprine, murine, and ovine species. Cell donors may vary in development and age.

In some cases, a brain cancer organoid may comprise recombinant or genetically-modified cells in place of or in addition to unmodified or wild-type ("normal") cells. For example, it can be advantageous in some instances to include recombinant and genetically-modified cells that produce recombinant cell products, growth factors, hormones, peptides or proteins for a continuous amount of time or as needed when biologically, chemically, or thermally signaled due to the conditions present in culture. Procedures for obtaining recombinant or genetically modified cells are generally known in the art, and are described in Sambrook et al, *Molecular Cloning, A Laboratory Manual*, Cold Spring Harbor Press, Cold Spring Harbor, N.Y. (1989), incorporated herein by reference.

In some cases, a brain cancer organoid comprises one or more cell types derived from a particular mammalian subject (e.g., a particular individual human subject). In some cases, one or more cell types derived from the particular individual exhibit one or more specific phenotypes associated with or resulting from a particular disease or disorder of the particular mammalian subject. Subject-specific cells can be obtained or isolated from a target tissue of interest by biopsy or other tissue sampling methods. In some cases, subject-specific cells are manipulated in vitro prior to use in a tissue construct of the invention. For example, subject-specific cells can be expanded, differentiated, genetically modified, contacted to polypeptides, nucleic acids, or other factors, cryopreserved, or otherwise modified prior to use in a brain cancer organoid.

In other cases, the subject-specific cells are induced pluripotent stem cells obtained by reprogramming somatic cells of the subject according to methods known in the art. See, for example, Yu et al., *Science* 324(5928):797-801 (2009); Chen et al., *Nat Methods* 8(5):424-9 (2011); Ebert et al., *Nature* 457(7227):277-80 (2009); Howden et al., *Proc Natl Acad Sci USA* 108(16):6537-42 (2011). Human induced pluripotent stem cells allow modeling of drug responses in a genetically diverse population of individuals, including those individuals with genetic diseases. Even the safest drugs may cause adverse reactions in certain individuals with a specific genetic background or environmental history. By way of non-limiting example, brain cancer organoids comprising cells derived from subject-specific iPSCs obtained from an individual having known susceptibilities or resistances to various drugs or diseases will be useful to identify genetic factors or epigenetic influences that contribute to variable drug responses.

In some cases, the hydrogel further comprises isolated biological components. As used herein, an "isolated" biological component (such as a protein, nucleic acid, or organelle) has been substantially separated or purified away from other biological components in a cell in which the component naturally occurs, such as chromosomal and extra-chromosomal DNA and RNA, proteins, and organelles. As used herein, the term "isolated protein" includes proteins purified by standard purification methods. The term also embraces proteins prepared by recombinant expression in a host cell, as well as chemically synthesized proteins, or fragments thereof.

It will be appreciated that brain cancer organoids of this disclosure can be modified in various ways to obtain organoids having different configurations or morphologies. For example, by seeding a hydrogel with a larger or smaller population of cells, and, consequently, altering the number, size, and composition (e.g., identity) of neuron and/or glial cell populations. Likewise, cellular components or other materials used to obtain a brain cancer organoid as described herein can be modified to, for example, vary material properties of the brain cancer organoid (e.g., vary crosslinking agent).

As used herein, the term "chemically defined" means that the identity and quantity of each component of a composition (e.g., a hydrogel) is known. An important goal in the fields of pluripotent stem cell culture and directed differentiation of pluripotent stem cells is to develop culture materials and culture media that provide improved performance consistency and reproducibility. In some cases, a chemically defined hydrogel for use in a brain cancer organoid provided herein comprises a minimal number of defined components/ingredients.

Any appropriate method or methods can be used to confirm uniformity and the presence or absence of certain components in a substantially planar brain cancer organoid provided herein. Suitable methods for detecting the presence or absence of biological markers are well known in the art and include, without limitation, immunohistochemistry, qRT-PCR, RNA sequencing, and the like for evaluating gene expression at the RNA level. In some cases, methods such as immunohistochemistry are used to detect and identify cell types or biomolecules within a substantially planar brain cancer organoid. For example, whole tissue constructs or portions thereof can be stained for specific differentiation markers by immunohistochemistry. In some cases, it will be advantageous to perform dual-label immunofluorescence to assess the relative expression of individual marker proteins or to detect multiple progenitor or differentiated cell types within a construct. Appropriate primary and secondary antibodies are known and available to those practicing in the art. In addition, microarray technology or nucleic acid sequencing (e.g., RNA sequencing) can be used to obtain gene expression profiles for 3D brain cancer organoids of the invention. Myeloid markers and macrophage associated markers include, for example, CD14, CD16, CSFR-1, CD11b, CD206 (also known as macrophage mannose receptor or MMR), CD68, and CD163. Biological markers for microglia include antibodies having specificity to CD45, CD68, Iba1, TMEM119, or HLA-DR complex. Quantitative methods for evaluating expression of markers at the protein level in cell populations are also known in the art. For example, flow cytometry is used to determine the fraction of cells in a given cell population that express or do not express biological markers of interest.

Viability of cells within a substantially planar brain cancer organoid can be examined for changes in phenotype, organization, and the presence or absence of certain proteins using, for example, magnetic sorting, flow cytometry, immunofluorescence, bright-field microscopy, and electron microscopy. In some cases, it will be advantageous to fix or freeze the brain cancer organoid for histology or microscopy. For example, brain cancer organoids can be fixed in formalin or paraformaldehyde for plastic embedment and sectioning using routine methods. Scanning electron microscopy (SEM) is useful to detect and analyze the formation of tubular structures in brain cancer organoids. In particular, SEM can be used to study cross-sectioned organoids to detect the presence and arrangement of blood vessels (e.g., large vessels, small capillaries). In exemplary embodiments, confocal microscopy can reveal the distribution of cell types and vascular structures throughout a brain cancer organoid. In some cases, a three-dimensional assembly of images obtained by confocal microscopy is used to analyze the distribution and organization of various cells and structures.

Morphology also can be used to characterize culture components, but cells of different origins may share similar features and be difficult to distinguish using morphology alone. Where appropriate, excitatory and inhibitory synaptic potentials can be analyzed using, for example, extra- or intracellular recording techniques.

Methods

In another aspect, the present invention provides methods for producing and using brain cancer organoids for high throughput screening of candidate test substances and identifying agents having anti-cancer and, preferably, anti-metastatic activity. Such agents may be used to inhibit metastatic spread of cancer cells in subjects having cancer. In addition, the methods may be used to screen for nucleic acid molecules with anti-metastatic potential. For example, antisense and ribozyme molecules may be screened for their ability to inhibit metastasis. In exemplary embodiments, the methods employ brain cancer organoids of this disclosure for screening pharmaceutical agents, anti-cancer agents, or the like. For example, brain organoids comprising a plurality of cancer cells or a tumor can be contacted with a test substance and the contacted organoid can be studied to detect a change in a biological property of the cancer cells or tumor in response to exposure to the test substance.

Advantages of the screening methods provided herein are multifold and include the ability to rapidly screen test substances for anti-cancer or anti-metastatic activity without having to wait for a metastasis to occur in a subject. Indeed, the in vitro screening methods can be conducted without the need for a human subject or animal models. The methods can be conducted economically (e.g., using multi-well plates that require minimal amounts of a test substance and relatively inexpensive hydrogel materials) and are readily adapted to high throughput methods (e.g., using robotic or other automated procedures).

In some cases, the methods comprise contacting a substantially homogeneous cancer cell population to a vascularized brain organoid as described herein. The cancer cell-seeded brain organoid is cultured under conditions that promote cancer cell proliferation as evidenced by positive controls using cancer cells that demonstrably proliferate under the culture conditions. Culturing under such conditions produces a vascularized brain cancer organoid comprising a plurality of cancer cells, whereby the cancer cells may form a tumor. Preferably, the culture conditions are physiological conditions (e.g., at physiological pH and temperature (about 37° C.)). The cancer cell and/or tumor-containing brain organoid is treated with a test substance. In these methods, there is no particular limitation on the method for treating a cancer cell population or tumor contained in the brain organoid with a test substance. For example, treatment with the test substance can be carried out by adding a test substance to a cell culture medium in which the brain organoid is cultured. As described herein, the methods of this disclosure are advantageous over standard in vitro and in vivo methodologies for drug discovery screens (e.g., screening patient-derived xenografts). In particular, the methods described herein provide sensitive, reproducible, and quantifiable methods for screening test substances. The methods are better alternatives to in vivo animal assays which are quantifiable assays but are error-prone, require a large number of animals, and are not easily standardized between laboratories or scalable for high-throughput screening. Shortcomings of animal-based assays have prompted regulatory agencies, including the Food and Drug Administration (FDA) and the United States Department of Agriculture, to promote the development of cell-based models comprising more physiologically relevant human cells and having the sensitivity and uniformity necessary for large-scale, quantitative in vitro modeling and screening applications (National Institutes of Health, 2008).

Following exposure to the test substance, a change in a biological property of the cancer cells or tumor treated with the test substance is then detected. Such a change in a biological property includes, for example, a change in a tissue structure characteristic of the process of cancer progression of the cancer cells or tumor, and a change in the expression of a DNA, RNA, protein, or metabolite in the cancer cells or tumor. A change in a biological property can be detected, for example, by the following methods. Observations to detect characteristic structures of tissues or cell lines during cancer progression, including tumor formation, can be achieved by performing hematoxylin and eosin (H&E) staining and/or immunohistochemistry (IHC) with, for example, detectably labeled antibodies. The expression of DNAs, RNAs, proteins, peptides, and metabolites can be assessed by conventional expression assessment methods. RNAs include microRNAs, siRNAs, tRNAs, snRNAs, mRNAs, and non-coding RNAs. For example, mRNAs of a gene are extracted according to a conventional method. Using the mRNAs as a template, the transcriptional level of the gene can be determined using the Northern hybridization or RT-PCR method. DNA array techniques can also be used to determine the expression level of the gene. Alternatively, fractions containing a protein encoded by a gene are collected according to a conventional method. The translational level of the gene can be determined by detecting the protein expression by an electrophoresis method such as SDS-PAGE. The translational level of a gene can also be determined by performing the Western blotting method using an antibody against a protein and detecting the protein expression.

Detecting a positive or negative change in viability or proliferation of cancer cells in the brain cancer organoid can comprise detecting at least one effect of a test substance by performing a method such as RNA sequencing, gene expression profiling, transcriptome analysis, metabolome analysis, detecting reporter or sensor, protein expression profiling, Forster resonance energy transfer (FRET), metabolic profiling, and microdialysis. Test substances can be screened for effects on gene expression in the contacted brain cancer organoid, where differential gene expression as compared to an uncontacted brain cancer organoid is detected.

Depending on the change in a biological property, or degree of change in a biological property, a test substance may be identified as useful as an anti-cancer agent or agent for suppressing metastasis or recurrence. For example, when tumor formation is not detected or the size of tumor is reduced following exposure to the test substance, the test substance is expected to be useful as a pharmaceutical agent having the activity of suppressing cancer progression, metastasis, or recurrence (for example, an anti-cancer agent or an agent for suppressing metastasis or recurrence). In other cases, an agent is identified as having anti-cancer activity if the agent reduces proliferation or life span of cancer cells or has a negative impact on the morphology of cancers cells in the contacted brain cancer organoid, A test substance that exhibits one or more of such anti-cancer activities can be selected as an effective substance that may be used to treat or prevent cancerous diseases. That is, pharmaceutical agents obtained by the screening methods are not particularly limited, and can be used as an anti-cancer agent, or an agent for suppressing metastasis or recurrence.

As used herein, "test substances" are not particularly limited and include, for example, single compounds such as natural compounds, organic compounds, inorganic compounds, proteins, antibodies, peptides, and amino acids, as well as compound libraries, expression products of gene libraries, cell extracts, cell culture supernatants, products of fermenting microorganisms, extracts of marine organisms, plant extracts, prokaryotic cell extracts, unicellular eukaryote extracts, and animal cell extracts. These may be purified products or crude purified products such as extracts of plants, animals, and microorganisms. Also, methods for producing test substances are not particularly limited; test substances may be isolated from natural materials, synthesized chemically or biochemically, or prepared by genetic engineering. "Test substances" also encompass mixtures of the above-mentioned substances.

In exemplary embodiments, a substantially planar brain cancer organoid provided herein is used to screen for new anti-cancer or anti-metastatic agents, or to evaluate and/or characterize candidates for anti-cancer or anti-metastatic agents. Agents identified by a method of this disclosure can be used, e.g., for the prevention or for the treatment of cancer metastasis and/or for the inhibition of growth of primary tumors caused by the seeding of the tumors with metastasized cells from the same or from a different tumor. As used herein, "anti-cancer activity" refers to the capacity of an agent to eliminate (cure) or to retard the growth and spread (remission) of cancer cells. Generally, an agent having anti-cancer activity will possess primary cytotoxic activity, thus effecting a direct kill on the cancer cells, or can stimulate the body's natural immunity, thus indirectly effecting cancer cell death. As used herein, "anti-metastatic activity" refers to anti-cancer activity that inhibits, in whole or in part, or retards the seeding of a metastatic cell to a tumor in a subject, or to inhibit the seeding in vitro of a metastatic cell to a colony of tumor cells (e.g., to a colony of cells from which the metastatic cell originated, or to a colony of different tumor or metastatic cells). The term "anti-metastatic" encompasses agents that can inhibit cancer metastasis, whereby a metastatic cancer cell is inhibited from seeding at a new site, at an established metastatic site, or into a primary tumor. An agent having anti-metastatic activity may function to inhibit metastasis at any of a variety of steps in metastatic progression. For example, it may result in the delayed appearance of secondary tumors, slowed development of primary or secondary tumors, decreased occurrence of secondary tumors, slowed or decreased severity of secondary effects of disease, arrested tumor growth and regression of tumors, among others. In the extreme, complete inhibition is referred to herein as prevention (e.g., virtually complete inhibition, no metastasis if it had not occurred, no further metastasis if there had already been metastasis of a cancer, or virtually complete inhibition of the growth of a primary tumor caused by re-seeding of the tumor by a metastasized cell).

In exemplary embodiments, such screening methods comprise contacting one or more test candidates having anti-cancer or anti-metastatic activity to a substantially planar brain cancer organoid and detecting a positive or negative change in a biological property or activity such as, without limitation, gene expression, protein expression, cell viability, and cell proliferation. The manner in which a test compound has an effect on a particular biological activity of cells in the brain cancer organoid will depend on the nature of the test compound, the composition of the tissue construct, and the particular biological activity being assayed. However, methods of the present invention will generally include the steps of (a) culturing a brain cancer organoid as provided herein with a test anti-cancer or anti-metastasis agent, (b) assaying a selected biological activity of the brain cancer organoid, and (c) comparing values determined in the assay to the values of the same assay performed using a substantially planar brain cancer organoid having the same composition of the assayed brain cancer organoid but cultured in the absence of the test anti-cancer/anti-metastasis agent and/or in the presence of a control agent, positive and negative controls for cancer cell growth, and other appropriate controls.

In exemplary embodiments, detecting and/or measuring a positive or negative change in a level of expression of at least one gene following exposure (e.g., contacting) of a substantially planar neural construct to a test compound comprises whole transcriptome analysis using, for example, RNA sequencing. In such cases, gene expression is calculated using, for example, data processing software programs such as Light Cycle, RSEM (RNA-seq by Expectation-Maximization), Excel, and Prism. See Stewart et al., *PLoS Comput. Biol.* 9:e1002936 (2013). Where appropriate, statistical comparisons can be made using ANOVA analyses, analysis of variance with Bonferroni correction, or two-tailed Student's t-test, where values are determined to be significant at $P<0.05$. Any appropriate method can be used to isolate RNA or protein from neural constructs. For example, total RNA can be isolated and reverse transcribed to obtain cDNA for sequencing.

Test compounds that are suitable for screening according to the methods provided herein include any for which one wishes to determine the effect the compound has on the brain of a mammal. Ideally, test compounds cover a range of potential cell toxicities. Test compounds can include FDA-approved and non-FDA-approved drugs (including those that failed in late stage animal testing or in human clinical trials) having known or unknown toxicity profiles. Test substances can be dissolved in a solvent such as, for example, dimethyl sulfoxide (DMSO) prior to contacting to a brain cancer organoid provided herein.

Pharmaceutical agents selected as having anti-cancer or anti-metastatic activity accordingly to the screening methods of this disclosure may be further screened as necessary by conducting additional drug effectiveness tests and safety tests, and further conducting clinical tests in human cancer patients.

Articles of Manufacture

In another aspect, this disclosure provides kits for preparing substantially planar brain organoids and substantially planar brain cancer organoids as described herein. In some cases, the kit comprises (a) a substantially planar vascularized brain organoid obtain by (i) contacting a mixed human cell population comprising neural progenitor cells, endothelial cells, pericytes, and microglia to a substantially planar hydrogel comprising an RGD-containing peptide and a matrix metalloproteinase (MMP)-sensitive peptide; and (ii) culturing the contacted hydrogel for 7 days until a substantially planar hydrogel comprising neurons, glia, and vasculature is obtained; and (b) instructions for contacting the vascularized brain organoid of (a) with cancer cells obtained from a subject. In some cases, the kit further comprises instructions for using the prepared brain organoid for screening test substances for those that exert a particular effect on the cancer cells (e.g., anti-cancer activity, anti-metastatic activity).

Nucleic acids and/or other constructs of the invention may be isolated. As used herein, "isolated" means to separate from at least some of the components with which it is usually associated whether it is derived from a naturally occurring source or made synthetically, in whole or in part.

The terms "protein," "peptide," and "polypeptide" are used interchangeably herein and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. A protein may comprise different domains, for example, a nucleic acid binding domain and a nucleic acid cleavage domain. In some embodiments, a protein comprises a proteinaceous part, e.g., an amino acid sequence constituting a nucleic acid binding domain.

Nucleic acids, proteins, and/or other compositions (e.g., cell population) described herein may be purified. As used herein, "purified" means separate from the majority of other compounds or entities, and encompasses partially purified or substantially purified. Purity may be denoted by a weight by weight measure and may be determined using a variety of analytical techniques such as but not limited to mass spectrometry, HPLC, etc.

In interpreting this disclosure, all terms should be interpreted in the broadest possible manner consistent with the context. Unless defined otherwise, all technical and scientific terms used herein have the same meaning as commonly understood by one of ordinary skill in the art to which the invention belongs. It is understood that certain adaptations of the invention described in this disclosure are a matter of routine optimization for those skilled in the art, and can be implemented without departing from the spirit of the invention, or the scope of the appended claims.

So that the compositions and methods provided herein may more readily be understood, certain terms are defined:

As used in this specification and the appended claims, the singular forms "a," "an," and "the" include plural references unless the context clearly dictates otherwise. Any reference to "or" herein is intended to encompass "and/or" unless otherwise stated.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

The terms "comprising", "comprises" and "comprised of" as used herein are synonymous with "including", "includes" or "containing", "contains", and are inclusive or open-ended and do not exclude additional, non-recited members, elements, or method steps. The phraseology and terminology used herein is for the purpose of description and should not be regarded as limiting. The use of "including," "comprising," "having," "containing," "involving," and variations thereof, is meant to encompass the items listed thereafter and additional items. Embodiments referenced as "comprising" certain elements are also contemplated as "consisting essentially of" and "consisting of" those elements. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

The terms "about" and "approximately" shall generally mean an acceptable degree of error for the quantity measured given the nature or precision of the measurements. Typical, exemplary degrees of error are within 10%, and preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The invention will be more fully understood upon consideration of the following non-limiting Examples. It is specifically contemplated that the methods disclosed are suited for pluripotent stem cells generally. All papers and patents disclosed herein are hereby incorporated by reference as if set forth in their entirety.

EXAMPLES

Example 1—Self-Assembled Human Induced Pluripotent Stem Cell-Derived Brain Organoids on PEG Hydrogels for Modeling Melanoma Metastasis Brain metastases occur in up to 43% of cutaneous melanoma patients in the clinic, and has been found in 75% of autopsies[1]. The standard for assessing drug efficacy for metastatic melanoma is the direct patient response to treatment. In order to save the patient from enduring multiple trial-and-error treatments, alternative models are necessary. Currently, there is significant interest in patient derived xenografts (PDX), in which a biopsy of the patient's tumor is implanted into an immune-deficient mouse and screened for various treatments. While PDXs have shown some success in determining tumor response to therapeutics, it is slow, expensive and is conducted in a rodent microenvironment rather than a human[2]. It is hypothesized that engineered brain organoids may be a better alternative in vitro environment to study cancer metastasis and drug response, while also having the potential to be used as a high-throughput human screening model. As demonstrated in this example, human induced pluripotent stem cell-derived brain organoids were self-assembled on PEG hydrogels (FIG. 1) and assessed for (1) their ability to recapitulate the brain microenvironment better than other organoid models and (2) their potential to be used as a model of melanoma metastasis.

Materials and Methods

Human induced pluripotent stem cells (IPSCs, WTC11) were expanded in E8 media (Life Technologies) and differentiated into neural progenitor cells (NPCs), endothelial cells (ECs), pericytes (PCs) and microglia as previously described[3]. A 96 well plate was coated with a PEG thiolene hydrogel made using 40% 8 arm PEG norbornene (tripentaerythritol) (JenKem Technology # A10037-10) modified with the 60% crosslinked Tryp-MMP peptide KCGGPQGIWGQGCK (SEQ ID NO:1, GenScript)), 2 mM CRGDS peptide (GenScript), and 0.05% Irgacure D2959 ("I2959") (Sigma #410896). 8.5 µl of the PEG hydrogel was added to each well of a 96-well U-bottomed tissue culture plate (Sigma # Z707880-108EA). The gels were incubated overnight at 37° C., 5% $CO_2$ in DMEM/F12 (HyClone # SH3002301) culture medium to swell the gels.

For organoid generation, the following cells were added to each well of a 96-well tissue culture plate: $1 \times 10^5$ neural progenitor cells (NPCs), $8 \times 10^4$ endothelial cells (ECs), $1.6 \times 10^4$ pericytes (PCs), and $2.5 \times 10^3$ microglia were added. PEG organoids were cultured in N2B27 (DF3S medium supplemented with 1:100 Glutamax, MEM NEAA, N2 and 1:50 B27 (Gibco)) for up to 21 days. Concurrently, Matrigel® brain organoids comprising WTC-11-derived cells were developed as previously described.

Cell-seeded hydrogels were screened for organoid formation to determine the optimal PEG hydrogel formulation for the production of planar organoids.

To investigate the initial effect of melanoma on the organoid cells, metastatic melanoma cells (A375-eGFP-Puro, Imanis) were co-cultured with monolayer organoid cells for 48 hours. Organoids were assessed by immunofluorescence for expression of markers for endothelial cells (CD31), NPCs (β3tubulin), pericytes (PDGRFβ), and microglia (Iba1).

Results

Figures 2A, 2B, 2C, 2D, 2E:
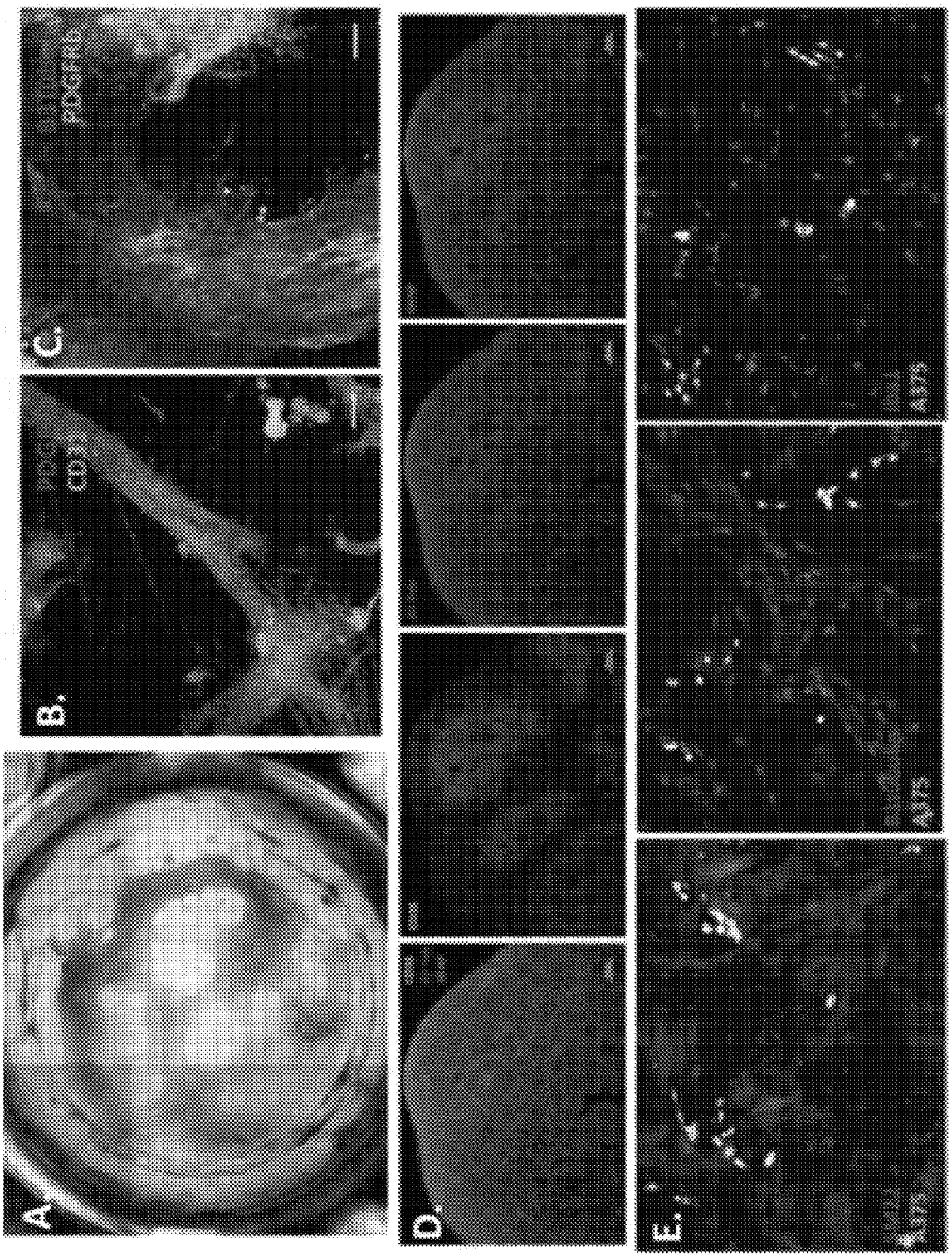
FIGS. 2A-2E are images demonstrating the presence of vasculature, neural networks, and GFP-labeled metastatic melanoma cells in a self-assembled planar brain organoid. (A) Planar PEG organoid. Immunofluorescent ("IF") images of vasculature (B) and neural network (C) in PEG organoids. (D) IF images of Matrigel® organoids. (E) A375-GFP co-culture with organoid cells.

After 21 days, a self-assembled planar brain organoid was formed (FIG. 2A). IF images show the presence of vasculature (FIG. 2B), where tubules were formed within the brain organoid and stained positively for the pericyte marker PDGFRβ and the endothelial marker CD31. The interaction between the neural network and the vasculature was visualized by positive staining of the neural marker β3tubulin and pericyte marker PDGFRβ (FIG. 2C). Additionally, microglia were also found in the organoids (Iba1, FIG. 2E). In order to determine a method for deriving brain organoids that best recapitulates the brain, the PEG organoids were compared to Matrigel® organoids. While, the Matrigel® organoids were also positive for the neural markers βtubulin and GFAP, there was a lack of CD31 and no presence of a vascularized network (FIG. 2D). These results suggest that PEG organoids better recapitulate the brain microenvironment, and therefore, are more suitable for disease modeling. In a preliminary co-culture study, metastatic melanoma cells (A375-eGFP-Puro) did not have an initial effect on organoid cell viability (FIG. 2E). This result is important for future studies focused on investigating tumor formation, cellular function, and drug response.

In summary, this example demonstrates assembly of an iPSC-derived vascularized brain organoid on PEG hydrogels. Unlike Matrigel®-based organoids, PEG organoids showed vascularization throughout, as well as microglia, which is important for establishing an immune response. An initial study showed the ability to co-culture metastatic melanoma cells with organoid cells, and studies of the growth and behavior of melanoma cells when infiltrating mature organoids are ongoing. Overall, PEG brain organoids offer an alternative in vitro model of metastatic melanoma that is suitable for high-throughput drug screening.

TABLE 1

An exemplary protocol for generating organoids from differentiated cells

A. Day −9 to −7: Thaw differentiated cells to use for organoid generation 7 to 9 days before required to ensure the cells have time to proliferate. Cells differentiated from iPSC line WTC-11 (Coriell Institute #GM25256) can be substituted for other iPSC-derived cells.
  i. Thaw 2 million WTC-11-derived neural progenitor cells (NPC) around days 32 to 35 of differentiation into a 10 cm Matrigel ® coated dish in N2B27(F) media.
  ii. Thaw 4 million passage 1 WTC-11-derived endothelial cells (EC) into a 10 cm Matrigel ® coated dish in E7V media (see Table 5 below).
  iii. Thaw 1 million passage 2 WTC-11-derived pericyte cells (PC) at day 9 or 10 of differentiation into a 10 cm dish pre-coated with 0.25 µg/cm$^2$ of a 1:1 mixture of Fibronectin (Corning #356008) and Collagen IV (Corning #354245) in PM media.
  iv. Thaw 1 million WTC-11-derived microglia (MG) into 4 wells of a 6 well low attachment plate (Corning #3471) in PMG medium (formulation in Table 4).
B. Re-feed the cells every 2 days with their respective media other than the MG. For the MG, carefully add 1 ml of PMG media to each well without removing the existing media to prevent the MG from detaching from the plate.
C. Day −1: On the day before generation of the organoids, produce PEG hydrogels. The working concentrations for the hydrogels are 8 arm PEG norbornene (tripentaerythritol) (JenKem Technology #A10037-10) 40 mg/ml, Tryp-MMP (GenScript) 60%, CRGDS (GenScript) 2 mM and Irgacure D2959 (Sigma #410896) 0.05%. Plate 8.5 µl per well of the PEG hydrogel to a 96-well U bottomed plate (Sigma #Z707880-108EA). The PEG hydrogel volume should be increased or decreased depending on the well size used. Incubate the gels overnight at 37° C., 5% $CO_2$ in DMEM/F12 (HyClone #SH3002301) medium to swell the gels.
D. Day 0: Harvest the cells using Accutase (Corning #25-058-CI) for NPC, EC and MG, and using TrypLE (Gibco #12563029) for PC. Resuspend the cells in N2B27(NG) media and count.
E. Plate the cells onto the PEG gels giving a final volume of 200 µl.
  a. The cell numbers used for organoid generation for a 96-well plate are approximately $1 \times 10^5$ NPC cells, $8 \times 10^4$ EC cells, $1.6 \times 10^4$ PC, and $2.5 \times 10^3$ MG per well.
  b. The ratios of cell numbers should be maintained and the overall numbers increased or decreased for different well sizes.
F. Incubate the cells at 37° C., 5% $CO_2$ for 48 hours without any media changes to allow the cells to attach.
G. Day 2: After the 48 hour incubation period feed the cells daily by removing approximately half of the media (100 µl for a 96 well plate) and replace with fresh N2B27(NG).
H. The organoids should be allowed to mature for at least 7 days to allow network formation. After this point other cell types, such as cancer cells (GFP positive or label free), can be added at various densities.
I. The organoids can be maintained for as long as necessary and various assays carried out such as
  a. Live imaging
  b. Fixing for immunofluorescent staining
  c. RNA extraction
  d. Addition of drugs
  e. ELISA assays on media samples saved from various time points throughout the study

TABLE 2

An exemplary alternative protocol for generating organoids from differentiated cells A. Day −9 to −7: Thaw differentiated cells to use for organoid generation 7 to 9 days before required to ensure the cells have time to proliferate. Cells differentiated from iPSC line WTC-11 (Coriell Institute #GM25256) can be substituted for other iPSC-derived cells.
  v. Thaw 2 million WTC-11-derived neural progenitor cells (NPC) around days 32 to 35 of differentiation into a 10 cm Matrigel ® coated dish in N2B27(F) media.
  vi. Thaw 4 million passage 1 WTC-11-derived endothelial cells (EC) into a 10 cm Matrigel ® coated dish in E7V media.

TABLE 2-continued

An exemplary alternative protocol for generating
organoids from differentiated cells

- vii. Thaw 1 million passage 2 WTC-11-derived pericyte cells (PC) at day 9 or 10 of differentiation into a 10 cm dish pre-coated with 0.25 µg/cm$^2$ of a 1:1 mixture of Fibronectin (Corning #356008) and Collagen IV (Corning #354245) in PM media.
- viii. Thaw 1 million WTC-11-derived microglia (MG) into 4 wells of a 6 well low attachment plate (Corning #3471) in PMG medium (formulation in Table 4).
- B. Re-feed the cells every 2 days with their respective media other than the MG. For the MG, carefully add 1 ml of PMG media to each well without removing the existing media to prevent the MG from detaching from the plate.
- C. Day −1: On the day before generation of the organoids, produce PEG hydrogels. The working concentrations for the hydrogels are 8 arm PEG norbornene (tripentaerythritol) (JenKem Technology #A10037-10) 40 mg/ml, Tryp-MMP (GenScript) 60%, CRGDS (GenScript) 2 mM and Irgacure D2959 (Sigma #410896) 0.05%. Plate 10 µl per well of the PEG hydrogel to a 96-well Angiogenesis plate (Ibidi #89646). The PEG hydrogel volume should be increased or decreased depending on the well size used. Incubate the gels overnight at 37° C., 5% $CO_2$ in DMEM/F12 (HyClone #SH3002301) medium to swell the gels.
- D. Day 0: Harvest the ECs using Accutase (Corning #25-058-CI), and the PCs using TrypLE (Gibco #12563029). Resuspend the cells in E7V media and count.
- E. Plate the cells onto the PEG gels giving a final volume of 50 µl.
  - a. The cell numbers used for organoid generation for a 96-well Angiogenesis plate are approximately $2 \times 10^4$ ECs and $4 \times 10^3$ PCs.
  - b. The ratios of cell numbers should be maintained and the overall numbers increased or decreased for different well sizes.
- F. Incubate the cells at 37° C., 5% $CO_2$ for 48 hours without any media changes to allow the cells to attach.
- G. Day 2: After the 48 hour incubation period feed the cells daily by removing approximately half of the media (50 µl for a 96 well angiogenesis plate) and replace with fresh E7V.
- H. Day 7: After the vascularized network has matured for 7 days, the NPCs are added.
  - a. Harvest NPCs using Accutase. Resuspend NPCs in N2B27(NG) media and count.
  - b. For a 96 well angiogenesis plate, seed $2.5 \times 10^4$ NPCs per well.
  - c. Remove all media from the vascularized network on the PEG cells, and plate NPCs in N2B27(NG) at a final volume of 50 µl.
  - d. Incubate the cells at 37° C., 5% $CO_2$
- I. Day 8-11: Feed the cells daily by removing media and replacing with fresh N2B27(NG) (50 µl for a 96 well angiogenesis plate).
- J. Day 12: Add MG to the organoids
  - a. Harvest MG using Accutase. Resuspend MG in N2B27(NG) media and count.
  - b. For a 96 well angiogenesis plate, seed $6.25 \times 10^2$ MG per well.
  - c. Remove media from the organoids and plate MG in N2B27(NG) at a final volume of 50 µl.
  - d. Incubate the cells at 37° C., 5% $CO_2$
- K. Day 13-: Feed cells daily by removing media and replacing with fresh N2B27(NG) (50 µl for a 96 well angiogenesis plate).
- L. The organoids should be allowed to mature for at least 14 days to allow network formation. After this point other cell types, such as cancer cells (e.g., GFP/mCherry-positive or label-free cancer cells), can be added at various densities.
- M. The organoids can be maintained for as long as necessary and various assays carried out such as
  - a. Live imaging
  - b. Fixing for immunofluorescent staining
  - c. RNA extraction
  - d. Addition of drugs
  - e. ELISA assays on media samples saved from various time points throughout the study

TABLE 3

Exemplary Protocol for Immunofluorescent Staining of Whole Organoids

Carefully wash organoids twice with 1X phosphate buffered saline (PBS)
(Fisher Scientific #BP665-1) to remove any traces of the 4% PFA block.
Permeabilize with 0.25% Triton (Fisher Scientific #BP151-100) in 1X PBS for
45 mins at room temperature (RT).

TABLE 3-continued

Exemplary Protocol for Immunofluorescent Staining of Whole Organoids

Block overnight at 4° C. in blocking buffer, i.e., 10% Newborn Donkey Serum (NDS) (Fisher Scientific #50594380), 1% bovine serum albumin (BSA) (Fisher Scientific #BP1600-100), 0.25% Triton in 1 X PBS.
Remove blocking buffer from the wells.
Add diluted primary antibodies in antibody buffer, i.e., 1% NDS, 1% BSA, 0.25% Triton in 1X PBS and incubate for 72 hours at 4° C.
   a. Suggested antibodies include:
      i. Anti-CD31 Mouse (Dako #M0823) 1 in 200 dilution
      ii. Anti-VWF Mouse (Thermo #MA5-14029) 1 in 50 dilution
      iii. Anti-β3 Tubulin Chicken (Novus #NB100-1612) 1 in 1000 dilution
      iv. Anti-PDGFR3 Rabbit (Abcam #ab32570) 1 in 100 dilution
      v. Anti-Iba1 Goat (Abcam #ab5076) 1 in 500 dilution
Wash organoids 5 × 30 mins washes in 1X PBS.
Wash overnight in 1X PBS at 4° C.
Add secondary antibodies in antibody buffer for 24 hours in the dark at 4° C.
   b. Suggested secondary antibodies include:
      i. Donkey anti mouse 488 (life technologies #A21202) 1 in 200 dilution
      ii. Goat anti Chicken 647 (life technologies #A21449) 1 in 200 dilution
      iii. Donkey anti rabbit 568 (life technologies #A10042) 1 in 200 dilution
      iv. Donkey anti goat 647 (life technologies #A21447) 1 in 200 dilution
In the last hour of incubation add DAPI (Fisher Scientific #574810) at 5 µg/ml to the antibody solution.
Wash organoids 5 × 30 mins in 1X PBS.
Wash overnight in 1X PBS at 4° C.
Store in fresh PBS until organoids are imaged.

TABLE 4

Exemplary PEG Hydrogel Formulations

| PEG Conc. mg/ml | Tryp-MMP % Crosslinker | CRGDS peptide Conc. mM | I2959 Conc. % | Sheer Modulus Pa |
|---|---|---|---|---|
| 40 | 40 | 2 | 0.2 | 55 |
| 40 | 50 | 2 | 0.2 | 237 |
| 40 | 60 | 2 | 0.2 | 321 |
| 50 | 40 | 2 | 0.2 | 195 |
| 50 | 50 | 2 | 0.2 | 269 |
| 50 | 60 | 2 | 0.2 | 747 |
| 60 | 40 | 2 | 0.2 | 422 |
| 60 | 50 | 2 | 0.2 | 722 |
| 60 | 60 | 2 | 0.2 | 1488 |

TABLE 5

Organoid Culture Medium Formulations

| Medium Name | Base Medium | Components | Component Catalogue Numbers | Working Conc. | Stock Conc. | Dilution |
|---|---|---|---|---|---|---|
| N2B27 (NG) | DF3S Gibco ME110262L1 | N2 Supplement | Gibco #17502-048 | 1× | 100× | 100 |
| | | B27 Supplement | Gibco #17504-044 | 1× | 50× | 50 |
| | | MEM NEAA | Gibco #11-140-050 | 100× | 1× | 100 |
| | | Glutamax | Gibco #35-050-061 | 100× | 1× | 100 |
| PMG | IMDM Biowhittaker 12001-604 | Heat Inactivated FBS | Gibco 316-000-044 | 10% | 100% | 10 |
| | | IL1β | PeproTech #200-01B | 100 µg/ml | 10 ng/ml | 10000 |
| | | MCSF | R&D Systems #216-MC-025 | 200 µg/ml | 20 ng/ml | 10000 |
| N2B27 (F) | DF3S Gibco ME110262L1 | N2 Supplement | Gibco #17502-048 | 1× | 100× | 100 |
| | | B27 Supplement | Gibco #17504-044 | 1× | 50× | 50 |
| | | FGF2 | R&D Systems #233-FB-500/CF | 100 ng/ml | 100 µg/ml | 1000 |

TABLE 5-continued

Organoid Culture Medium Formulations

| Medium Name | Base Medium | Components | Component Catalogue Numbers | Working Conc. | Stock Conc. | Dilution |
|---|---|---|---|---|---|---|
| E7V | DF3S Gibco ME110262L1 | Insulin | Sigma I9278 | 20 µg/ml | 10 mg/ml | 500 |
| | | VEGFA165 | R&D systems #293-VE-500/CF | 50 ng/ml | 100 µg/ml | 2000 |
| | | Transferrin | R&D systems 42914-HT | 10.7 µg/ml | 100 mg/ml | 1000 |
| | | FGF2 | R&D Systems #233-FB-500/CF | 100 ng/ml | 100 µg/ml | 1000 |
| PM | PM ScienCell #1201 | FBS | ScienCell #0010 | 2% | 100% | 50 |
| | | PGS | ScienCell #1252 | 100× | 1× | 100 |

REFERENCES

1. Sampson J H. *Neurosurg.* 1998:88:11-20.
2. Long G V. *Lancet Onco* 2012:13:1087-95.
3. Schwartz M P. *PNAS.* 2015:11:12516-21.

Example 2—Effects of Hydrogel Stiffness on Organoid Morphology and Reproducibility On the day before generation of the organoids PEG hydrogels need to be produced. PEG hydrogels were prepared as in Table 4 and 8.5 µl plated per well to a 96 well U bottomed plate (Sigma # Z707880-108EA) and UV polymerized. The gels were incubated overnight at 37° C., 5% $CO_2$ in DME/F12 (HyClone # SH3002301) media to swell the gels. The following day, $1 \times 10^5$ NPC cells, $8 \times 10^4$ EC cells, $1.6 \times 10^4$ PC, and $2.5 \times 10^3$ MG were plated per well in N2B27(NG) media.

ARES rheometer was used to conduct a dynamic strain sweep test to assess the mechanical properties of hydrogel formulations. The PEG hydrogels were polymerized in a circular Teflon mold with 8 mm diameter and 1.2 mm depth. 5.5 g force was applied to the samples with parallel plate crossheads and run from 0.005% to 100% strain. The complex shear modulus was calculated as the average of measurements taken at 1 Hz, 2% to 20% strain.

Variations in shear modulus (hydrogel stiffness) result in morphological changes of the organoids. Folding can be observed starting at day 7 (FIG. 4), increasing on day 14 (FIG. 6) and the folding especially apparent by day 28 with some organoids becoming much more compact (FIG. 7). Hydrogels with "medium" stiffness, specifically the 321 Pa hydrogel, provide a planar organoid that is highly reproducible. The formulation of this hydrogel is as follows: 8 arm PEG norbornene (tripentaerythritol) (JenKem Technology # A10037-10) 40 mg/ml, Tryp-MMP (GenScript) 60%, CRGDS (GenScript) 2 mM, and Irgacure D2959 (Sigma #410896) 0.2% in PBS. This indicates that the stiffness of the gel combined with the cell composition is critical to producing planar reproducible organoids.

Example 3—Organoids Seeded With A375 Metastatic Melanoma Cells

Organoids were generated as previously described. Briefly, a monomer solution comprising an 8 arm PEG norbornene (tripentaerythritol) (JenKem Technology # A10037-10) 40 mg/ml, Tryp-MMP (GenScript) 60%, CRGDS (GenScript) 2 mM, and Irgacure D2959 (Sigma #410896) 0.05% in PBS was prepared, and 8.5µl plated per well to a 96 well U bottomed plate (Sigma # Z707880-108EA) and UV polymerized. The gels were incubated overnight at 37° C., 5% $CO_2$ in DME/F12 (HyClone # SH3002301) media to swell the gels. The following day, $1 \times 10^5$ NPC cells, $8 \times 10^4$ EC cells, $1.6 \times 10^4$ PC, and $2.5 \times 10^3$ MG were plated per well in N2B27(NG) media. Organoids were cultured for 14 days with media changes every day. At 14 days, GFP-labeled A375 metastatic melanoma cells (Imanis Cat # CL056) were added and co-cultured for 14 days with daily media changes of N2B27(NG). Organoids were fixed at day 28, stained for pericyte vasculature using an anti-PDGFRβ antibody, and imaged on a confocal microscope (Zeiss).

Figure 8:
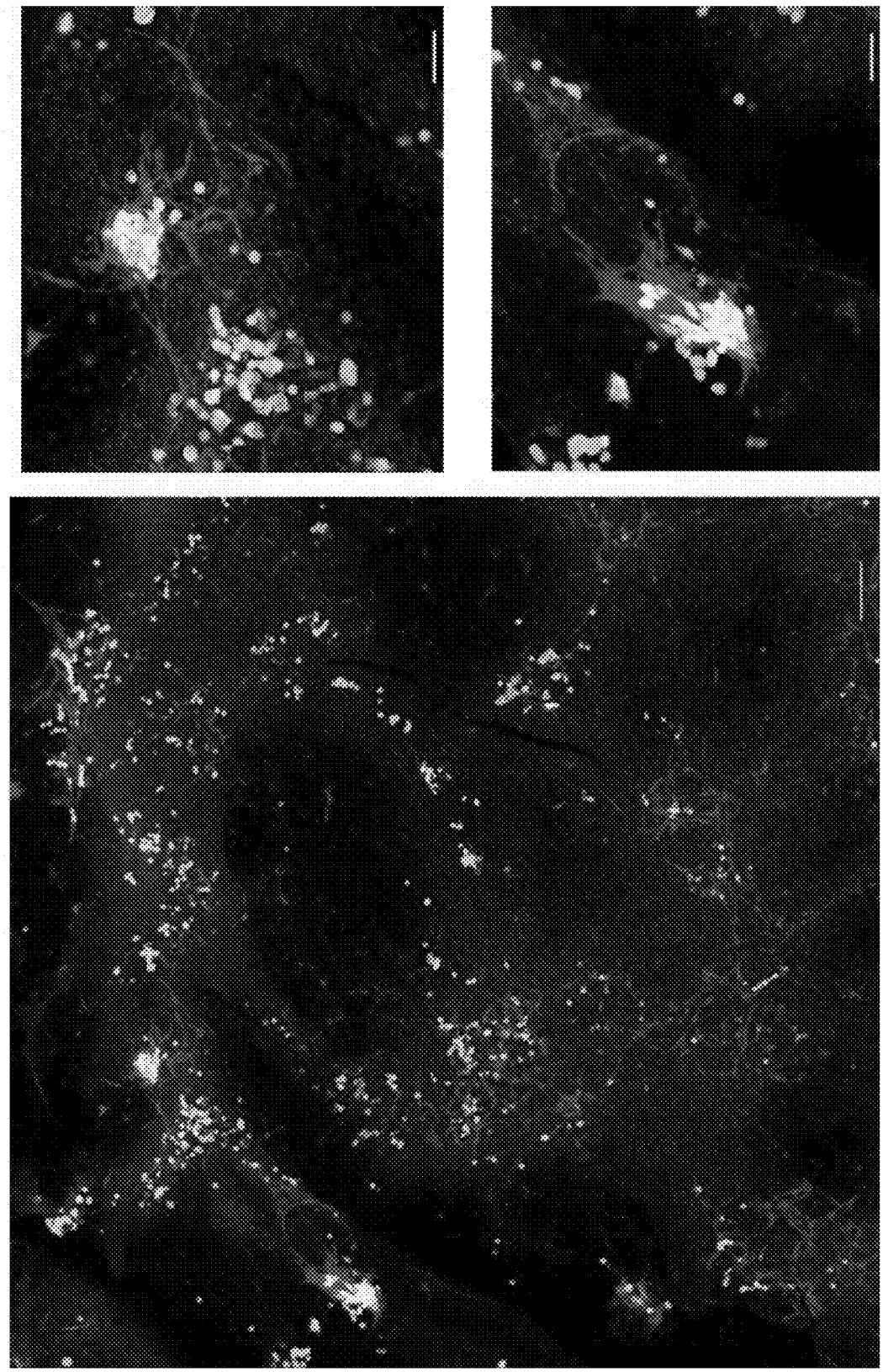
FIG. 8 provides images of Day 28 brain organoids demonstrating the presence of vasculature (PDGFRβ (red)) and GFP-labeled metastatic melanoma cells (green).

Images (FIG. 8) revealed the co-localization of A375 metastatic melanoma cells in areas of vasculature positively stained for PDGFRβ. A375 cells were found throughout the vasculature in round and spread morphology, with areas of A375 aggregates co-localized with high concentrations of PDGFRβ. A375 cells were not found in areas lacking vasculature (i.e., the absence of PDGFRβ), suggesting that they preferentially associate with the vasculature over the neural network.

We claim:

1. A method of producing a substantially planar vascularized brain cancer organoid, comprising
   (a) contacting a plurality of human cells to a substantially planar hydrogel, wherein the hydrogel comprises an RGD-containing peptide and a matrix metalloproteinase (MMP)-sensitive peptide, the plurality of human cells comprising neural progenitor cells, endothelial cells, pericytes, and microglia, wherein neural progenitor cells comprise approximately half of the plurality of cells, endothelial cells comprise approximately 40% of the plurality of cells, pericytes comprise approximately 8% of the plurality of cells and microglia comprise approximately 1% of the plurality of cells;
   (b) culturing the contacted hydrogel for at least 7 days until a hydrogel comprising neurons, glia, and vasculature is obtained;
   (c) contacting cancer cells to the cultured hydrogel of (b); and
   (d) culturing the cancer cell-contacted hydrogel under culture conditions that promote cancer cell proliferation, whereby a vascularized brain cancer organoid comprising a plurality of cancer cells is obtained.

2. The method of claim 1, wherein the plurality of cancer cells form a tumor.

3. The method of claim 1, wherein the cancer cells comprise lung cancer cells, breast cancer cells, melanoma, colon cancer cells, pancreatic cancer cells, or prostate cancer cells.

4. The method of claim 1, wherein the neural progenitor cells, endothelial cells, pericytes, or microglia are derived from human pluripotent stem cells.

5. The method of claim 1, wherein the hydrogel comprises polymerized polyethylene glycol (PEG).

6. The method of claim 1, wherein the hydrogel has a shear modulus of between about 100 Pa to about 1600 Pa.

7. The method of claim 1, wherein the RGD-containing peptide is selected from the group consisting of CRGDS (SEQ ID NO:2), RGDS (SEQ ID NO:3), RGDSC (SEQ ID NO:4), CCRGDS (SEQ ID NO:5), CCCRGD (SEQ ID NO:6), Ac-CRGDS (SEQ ID NO:7), CRGDS-CONH(2) (SEQ ID NO:8), and Ac-CRGDS-CONH(2) (SEQ ID NO:9).

8. The method of claim 1, wherein the MMP-sensitive peptide is SEQ ID NO:1.

9. A method of producing a substantially planar vascularized brain cancer organoid, comprising
   (a) on day zero, contacting a plurality of human cells to a substantially planar hydrogel, wherein the hydrogel comprises an RGD-containing peptide and a matrix metalloproteinase (MMP)-sensitive peptide, the plurality of human cells comprising one or more of human ECs and PCs at day zero;

(b) culturing the contacted hydrogel for about 6 to about 8 days, and then adding human NPCs to the cultured hydrogel;

(c) culturing the NPC-containing hydrogel of (b) for about 4 to about 6 days, and then adding human microglia (MG) to the cultured NPC-containing hydrogel;

(d) culturing the MG-containing hydrogel of (c) until a vascularized brain organoid comprising neurons, glia, and vasculature is obtained;

(e) contacting cancer cells to the brain organoid of (d); and (f) culturing the cancer cell-contacted brain organoid under culture conditions that promote cancer cell proliferation, whereby a vascularized brain cancer organoid comprising a plurality of cancer cells is obtained.

10. The method of claim 9, wherein the plurality of cancer cells form a tumor.

11. The method of claim 9, wherein the cancer cells comprise lung cancer cells, breast cancer cells, melanoma, colon cancer cells, pancreatic cancer cells, or prostate cancer cells.

12. The method of claim 9, wherein the neural progenitor cells, endothelial cells, pericytes, or microglia are derived from human pluripotent stem cells.

13. The method of claim 9, wherein the hydrogel comprises polymerized polyethylene glycol (PEG).

14. The method of claim 9, wherein the RGD-containing peptide is selected from the group consisting of CRGDS (SEQ ID NO:2), RGDS (SEQ ID NO:3), RGDSC (SEQ ID NO:4), CCRGDS (SEQ ID NO:5), CCCRGD (SEQ ID NO:6), Ac-CRGDS (SEQ ID NO:7), CRGDS-CONH(2) (SEQ ID NO:8), and Ac-CRGDS-CONH(2) (SEQ ID NO:9).

15. A method of producing a substantially planar vascularized brain cancer organoid, comprising:

(a) contacting a plurality of human cells to a substantially planar hydrogel, wherein the hydrogel comprises an RGD-containing peptide and a matrix metalloproteinase (MMP)-sensitive peptide, the plurality of human cells comprising neural progenitor cells, endothelial cells, pericytes, and microglia, wherein neural progenitor cells and the microglia are present in a ratio of approximately 40:1;

(b) culturing the contacted hydrogel for at least 7 days until a hydrogel comprising neurons, glia, and vasculature is obtained;

(c) contacting cancer cells to the cultured hydrogel of (b); and (d) culturing the cancer cell-contacted hydrogel under culture conditions that promote cancer cell proliferation, whereby a vascularized brain cancer organoid comprising a plurality of cancer cells is obtained.

16. The method of claim 15, wherein the plurality of cancer cells form a tumor.

\* \* \* \* \*

UNITED STATES PATENT AND TRADEMARK OFFICE
CERTIFICATE OF CORRECTION

| | |
|---|---|
| PATENT NO. | : 12,123,026 B2 |
| APPLICATION NO. | : 16/831017 |
| DATED | : October 22, 2024 |
| INVENTOR(S) | : Elizabeth Anne Aisenbrey et al. |

It is certified that error appears in the above-identified patent and that said Letters Patent is hereby corrected as shown below:

In the Specification

Column 20, Line 51, "βtubulin" should be --β3tubulin--.

Signed and Sealed this
Third Day of December, 2024

Katherine Kelly Vidal
*Director of the United States Patent and Trademark Office*